United States Patent [19]
Abrecht et al.

[11] Patent Number: 5,837,807
[45] Date of Patent: Nov. 17, 1998

[54] TETRAHYDRONAPHTHALENE COMPOUNDS

[75] Inventors: Christine Abrecht, Lengnau; Alfred Grieder, Sissach; Klaus Müller, Münchenstein; Daniel Obrecht, Basel, all of Switzerland

[73] Assignee: Hoffmann-La Roche Inc., Nutley, N.J.

[21] Appl. No.: 607,734

[22] Filed: Feb. 27, 1996

[30] Foreign Application Priority Data

Feb. 28, 1995 [CH] Switzerland ............... 00 567/95

[51] Int. Cl.$^6$ ............... C07K 4/00; C07K 5/12; C07D 285/00
[52] U.S. Cl. ............ 530/317; 530/326; 530/327; 530/328; 530/329; 530/330; 530/333; 530/335; 530/338; 540/455; 556/420; 560/10; 560/19; 560/28; 562/427; 562/428
[58] Field of Search ............... 530/300, 317, 530/326, 327, 328, 329, 330, 335, 337; 540/455; 560/10, 19, 28; 556/420; 562/427, 458

[56] References Cited

FOREIGN PATENT DOCUMENTS 0 592 791  4/1994  European Pat. Off. .
0 640 618  3/1995  European Pat. Off. .

OTHER PUBLICATIONS

Callahan, et al. The Use of γ–Turn Mimetics to Define Peptide Secondary Structure, Tetrahedron vol. 49, No. 17 pp. 3479–3488 (1993).
Callahan, et al. Design and Synthesis of a C$_7$ Mimetic for the Predicted γ–Turn Conformation Found in Several Constrained RGD Antagonists[1], J. Med. Chem, vol. 35, pp. 3970–3972 (1992).

*Primary Examiner*—Ponnathapura Achutamurthy
*Attorney, Agent, or Firm*—George W. Johnston; William H. Epstein; Briana C. Buchholz

[57] ABSTRACT

This invention is directed to tetrahydronaphthalene compounds of the formula

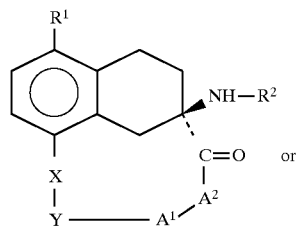

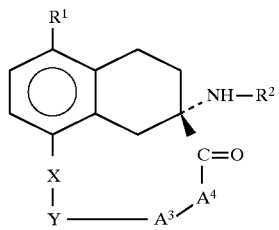

wherein $R^1$ is hydrogen, bromine, cyano, formyl, hydroxy, lower alkyl, lower alkenyl, lower alkynyl, lower alkoxy, aryloxy, lower aralkoxy or aryl; $R^2$ is an amino acid residue or a chain of 2 to 20 amino acid residues wherein reactive moieties in the side chains of the amino acid residue(s) is/are protected or unprotected, and wherein the amino group of the N-terminal amino acid is a free or protected amino group; $A^1$, $A^2$, $A^3$ and $A^4$ each are α-amino acid residues wherein $A^1$ and $A^2$ are in the L configuration and $A^3$ and $A^4$ are in the D configuration when the α-C atom of said α-amino acid residue is asymmetric; X is oxygen or sulphur; Y is a residue of the formula

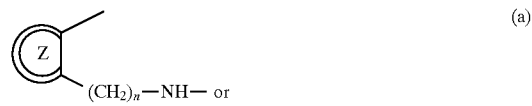

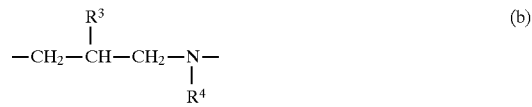

n is 0 or 1; $R^3$ is hydrogen or lower alkyl; $R^4$ is hydrogen or lower alkyl; and Z and the two C atoms together are an aromatic ring selected from the group of benzene, furan, thiophene, pyridine or pyrimidine, wherein said aromatic ring is substituted or unsubstituted; and salts thereof and their intermediates. The compounds are useful as mimetics of exposed helical domains of proteins in order to clarify their role with respect to interactions with other proteins or with DNA or RNA through α-helical conformation. They are therefore valuable aids in the determination of biologically active peptide sequences and are accordingly so-called "research tools". They are also potentially useful as medicaments.

47 Claims, 1 Drawing Sheet

REFERENCE PEPTIDE
50% HELICAL
NEUTRAL

PHENYL-C CAP
92% HELICAL
ACIDIC
81% HELICAL
NEUTRAL

TETRAHYDRONAPHTHALENE COMPOUNDS

SUMMARY OF THE INVENTION

The present invention is concerned with tetrahydronaphthalene compounds which are mimetics of domains of peptides or proteins which can interact with other proteins or with DNA or RNA through α-helical conformation. These tetrahydronaphthalene compounds have the general formula

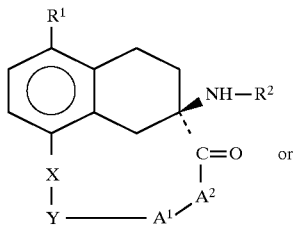

Ia

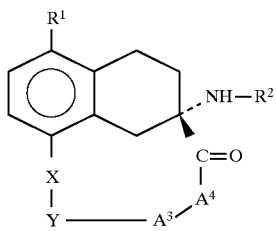

Ib wherein $R^1$ is hydrogen, bromine, cyano, formyl, hydroxy, lower alkyl, lower alkenyl, lower alkynyl, lower alkoxy, aryloxy, lower aralkoxy or aryl; $R^2$ is an amino acid residue or a chain of 2 to 20 amino acid residues wherein reactive moieties in the side chains of the amino acid residue(s) is/are protected or unprotected, and wherein the amino group of the N-terminal amino acid is a free or protected amino group; $A^1$, $A^2$, $A^3$ and $A^4$ each are α-amino acid residues wherein $A^1$ and $A^2$ are in the L configuration and $A^3$ and $A^4$ are in the D configuration when the α-C atom of said α-amino acid residue is asymmetric; X is oxygen or sulphur; Y is a residue of the formula

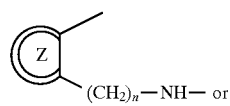

(a)

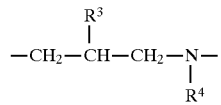

(b)

n is 0 or 1; $R^3$ is hydrogen or lower alkyl; $R^4$ is hydrogen or lower alkyl; and Z and the two C atoms together are an aromatic ring selected from the group of benzene, furan, thiophene, pyridine or pyrimidine, wherein said aromatic ring is substituted or unsubstituted; and salts thereof. Intermediates for these compounds are also part of this invention.

DETAILED DESCRIPTION OF THE INVENTION

Figure 1A:
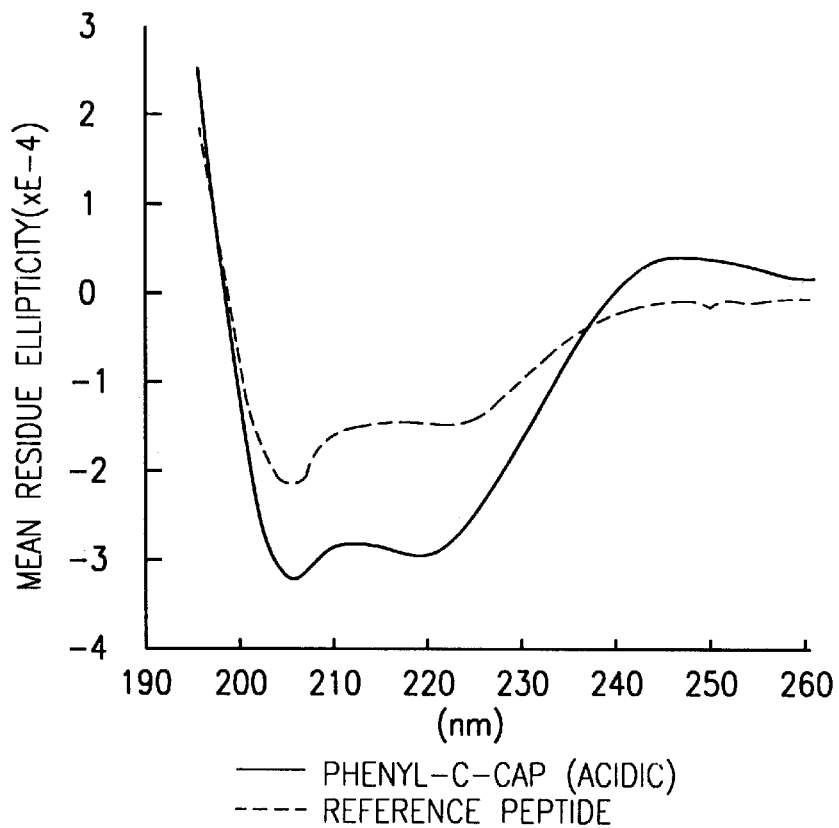
FIG. 1: shows a comparison of the helicity of a 9-residue polypeptide when that polypeptide contains a C-Cap of the configuration of formula Ia, and also without a C-Cap but with an Aib-(Ala)$_2$-NH—C$_6$H$_4$-I residue instead.

The present invention is concerned with tetrahydronapthalene compounds having the formula:

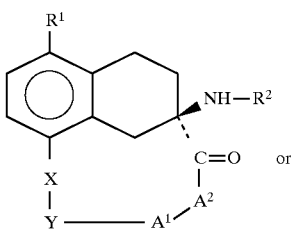

Ia

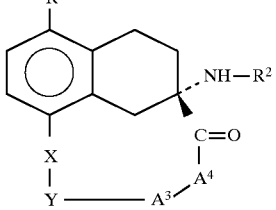

Ib wherein $R^1$ is hydrogen, bromine, cyano, formyl, hydroxy, lower alkyl, lower alkenyl, lower alkynyl, lower alkoxy, aryloxy, lower aralkoxy or aryl; $R^2$ is an amino acid residue or a chain of 2 to 20 amino acid residues wherein reactive moieties in the side chains of the amino acid residue(s) is/are protected or unprotected, and wherein the amino group of the N-terminal amino acid is a free or protected amino group; $A^1$, $A^2$, $A^3$ and $A^4$ each are α-amino acid residues wherein $A^1$ and $A^2$ are in the L configuration and $A^3$ and $A^4$ are in the D configuration when the α-C atom of said α-amino acid residue is asymmetric; X is oxygen or sulphur; Y is a residue of the formula

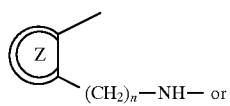

(a)

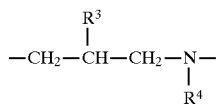

(b)

n is 0 or 1; $R^3$ is hydrogen or lower alkyl; $R^4$ is hydrogen or lower alkyl; and Z and the two C atoms together are an aromatic ring selected from the group of benzene, furan, thiophene, pyridine or pyrimidine, wherein said aromatic ring is substituted or unsubstituted; and salts thereof.

The compounds of general formulae Ia and Ib and their salts are novel. These compounds and salts, especially those which contain no protecting group(s), are valuable aids for determining biologically active peptide sequences and are therefore so-called "research tools"; they are, however, also potentially suitable as medicaments.

Objects of the present invention are the compounds of general formulae Ia and Ib and salts thereof, their manufacture, intermediates for their manufacture in particular intermediates of formulae IIa and b, IIIa and b, and IVa and b, and the use of compounds of general formulae Ia and Ib and of salts thereof as research tools.

A compound of this invention of formula Ia or Ib (and in addition as applicable of formulae IIb, IIIa, IIIb, IVa and IVb) may have $R^1$ as aryl. When $R^1$ is aryl, preferred are phenyl mono- or disubstituted by lower alkyl or lower alkoxy or phenyl substituted by lower alkylenedioxy.

For any compound of this invention, in particular formulae Ia and b, $R^2$ may be 9 to 15 amino acid residues in length, in particular 9, 12, or 15 residues. For any amino acid residues of $R^2$ which are α-amino acids, these amino acids are preferably in the L configuration when the α-C atom of said amino acid is asymmetric.

In particular, $R^2$ may comprise one or more residues selected from the group of L-alanine, L-glutamine, L-glutamic acid, L-isoleucine, L-leucine, L-lysine and 2-amino-2-methylpropionic acid.

For any compound of this invention, in particular of formula Ia or b, $A^1$ may be a residue of L-alanine, asparagine, aspartic acid, glutamine, glutamic acid, lysine or of 2-amino-2-methylpropionic acid and $A^3$ may be a residue of D-alanine, asparagine, aspartic acid, glutamine, glutamic acid or lysine or of 2-amino-2-methylpropioric acid; while $A^2$ may be a residue of L-alanine, asparagine, aspartic acid, glutamine, glutamic acid or lysine; and $A^4$ may be a residue of D-alanine, asparagine, aspartic acid, glutamine, glutamic acid or lysine. In preferred compounds of this invention, $A^1$ and $A^2$ are L-alanyl and $A^3$ and $A^4$ are D-alanyl, in particular where $R^2$ comprises the residues listed in the above paragraph.

In compounds of this invention, Y may be a residue of formula (b) or, preferably, of formula (a). When Y is a residue of formula (a), in particular Z and the two C atoms together may be benzene or pyrimidine.

Any compound of this invention, in particular of formula Ia or b, may have Y as residue of formula (a), in particular where n is 0 and Z and the two C atoms together are benzene. In particular, such compounds may have $A^1$–$A^4$ as the residues listed above while $R^2$ also comprises the residues listed above.

In any compound of this invention, in particular of formula Ia or b, X may be oxygen. In particular $R^1$ may be hydrogen and X may be oxygen. Specific compounds of this invention have the amino group of the N-terminal amino acid of $R^2$ as a protected amino group, with any protecting group as described below. Such a protected amino group may protected with para-bromo-benzoyl.

Preferred compounds of formula Ia or b of this invention therefore include the following: N-(4-Bromo-benzoyl)-L-alanyl-L-alanyl-2-methyl-alanyl-L-alanyl-L-alanyl-L-alanyl-L-alanyl-L-alanyl-L-alanine (12S,15S,18R)-(12,15-dimethyl-11,14,17-trioxo-10,11,12,13,14,15,16,17,18,19,20,21-dodecahydro-1,18-etheno-dibenz[b,n][1,5,8,11]oxatriazacyclopentadecin-18-yl)-amide.

N-(4-bromo-benzoyl)-L-alanyl-L-alanyl-2-methyl-alanyl-L-alanyl-L-alanyl-L-alanyl-L-alanyl-L-alanyl-L-alanine (12S,15S,18R)-(12,15-dimethyl-11,14,17-trioxo-10,11,12,13,14,15,16,17,18,19,20,21-dodecahydro-1,18-etheno-pyrido[2,3-b]benz[n][1,5,8,11]oxatriazacyclopentadecin-18-yl)-amide.
N-(4-bromo-benzoyl)-L-alanyl-L-alanyl-2-methyl-alanyl-L-alanyl-L-alanyl-L-alanyl-L-alanyl-L-alanyl-L-alanine (3S,7S,10S,13R)-(3,7,10-trimethyl-6,9,12-trioxo-3,4,5,6,7,8,9,10,11,12,13,14,19,20-tetradecahydro-13,15-etheno-2H-1,5,8,11-benzoxatriazacyclohexadecin-13-yl)-amide.
N-(4-bromo-benzoyl)-L-alanyl-L-alanyl-2-methyl-alanyl-L-alanyl-L-alanyl-L-alanyl-L-alanyl-L-alanyl-L-alanine (3S,7S,10S,13R)-(5-ethyl-3,7,10-trimethyl-6,9,12-trioxo-13,15-etheno-3,4,5,6,7,8,9,10,11,12,13,14,19,20-tetradecahydro-2H-1,5,8,11-benzoxatriazacyclohexadecin-13-yl)-amide.
N-(4-bromo-benzoyl)-L-alanyl-L-alanyl-2-methyl-alanyl-L-alanyl-L-alanyl-L-alanyl-L-alanyl-L-alanyl-L-alanine (13S,16S,19R)-(13,16-dimethyl-12,15,18-trioxo-11,12,13,14,15,16,17,18,19,20,21,22-dodecahydro-1,19-etheno-10H-dibenz[b,o][1,5,8,11]oxatriazacyclohexadecin-19-yl)-amide.

This invention also includes compounds of the formula

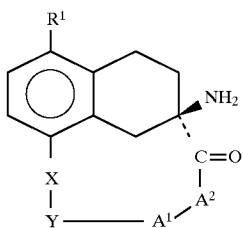

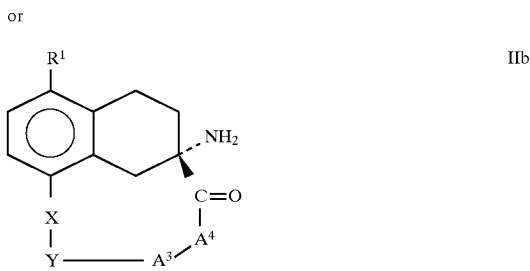

In these compounds, the substituents $R^1$, $A^1$, $A^2$, $A^3$, $A^4$, X, and Y are all as defined above in connection with the compounds of formulae Ia and Ib, including the most general definitions of the substituents and any more specific definitions. All such compounds are part of this invention.

In particular the compounds of formulae IIa and IIb of this invention include any compounds where $R^1$ is aryl and particularly where $R^1$ is phenyl mono- or disubstituted by lower alkyl or lower alkoxy or phenyl substituted by lower alkylenedioxy.

In compounds of formulae IIa and b, $A^1$ may be a residue of L-alanine, asparagine, aspartic acid, glutamine, glutamic acid, lysine or of 2-amino-2-methylpropionic acid; $A^3$, a residue of D-alanine, asparagine, aspartic acid, glutamine, glutamic acid or lysine or of 2-amino-2-methylpropionic acid; $A^2$, a residue of L-alanine, asparagine, aspartic acid, glutamine, glutamic acid or lysine; and $A^4$ a residue of D-alanine, asparagine, aspartic acid, glutamine, glutamic acid or lysine. In particular $A^1$ and $A^2$ may be L-alanyl and $A^3$ and $A^4$ may be D-alanyl.

Another compound of formulae IIa and b has Y as a residue of formula (a), n is 0 and Z and the two C atoms together as a benzene.

This invention also includes compounds of the formula

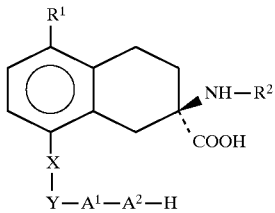

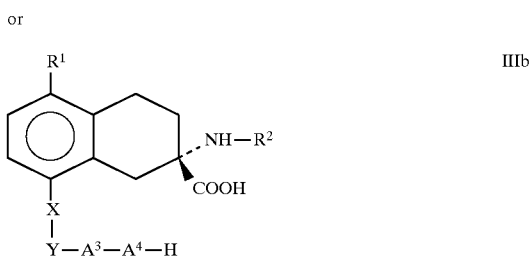

In these compounds, the substituents $R^1$, $R^2$, $A^1$, $A^2$, $A^3$, $A^4$, X, and Y are all as defined above in connection with the compounds of formulae Ia and Ib, including the most general definitions of the substituents and any more specific definitions. All such compounds are part of this invention.

In particular the compounds of formulae IIIa and IIIb of this invention include any compounds where $R^1$ is aryl and particularly where $R^1$ is phenyl mono- or disubstituted by lower alkyl or lower alkoxy or phenyl substituted by lower alkylenedioxy.

Compounds of formulae IIIa and b may have $R^2$ as 9 to 15 amino acid residues, preferably 9, 12 or 15 amino acid residues, and where any amino acid residues of $R^2$ which are α-amino acids, are preferably in the L configuration when the α-C atom of said amino acid is asymmetric. Specifically, $R^2$ may comprise one or more residues selected from the group of L-alanine, L-glutamine, L-glutamic acid, L-isoleucine, L-leucine, L-lysine and 2-amino-2-methylproprionic acid.

In compounds of formulae IIIa and b, $A^1$ may be a residue of L-alanine, asparagine, aspartic acid, glutamine, glutamic acid, lysine or of 2-amino-2-methylpropionic acid; $A^3$, a residue of D-alanine, asparagine, aspartic acid, glutamine, glutamic acid or lysine or of 2-amino-2-methylpropionic acid; $A^2$, a residue of L-alanine, asparagine, aspartic acid, glutamine, glutamic acid or lysine; and $A^4$ a residue of D-alanine, asparagine, aspartic acid, glutamine, glutamic acid or lysine. in particular $A^1$ and $A^2$ may be L-alanyl and $A^3$ and $A^4$ may be D-alanyl.

Any compound of formulae IIIa and b may have Y as a residue of formula (a), n as 0 and Z and the two C atoms together as a benzene.

This invention also includes compounds of the formula

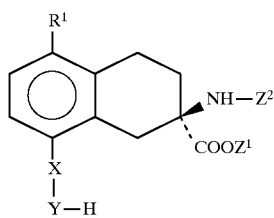

IVa or

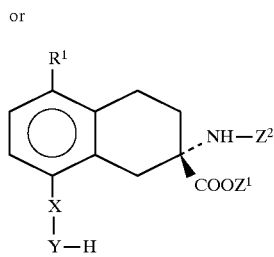

IVb

In these compounds, the substituents $R^1$, X, and Y are all as defined above in connection with the compounds of formulae Ia and Ib, including the most general definitions of the substituents and any more specifc definitions. All such compounds are part of this invention.

In particular the compounds of formulae IVa and IVb of this invention include any compounds where $R^1$ is aryl and particularly where $R^1$ is phenyl mono- or disubstituted by lower alkyl or lower alkoxy or phenyl substituted by lower alkylenedioxy.

Any compound of formulae IVa and b may have Y as a residue of formula (a), n as 0 and Z and the two C atoms together as a benzene.

In compounds of formulae IVa and b, $Z^1$ is a carboxyl protecting group and $Z^2$ is an amino protecting group.

Preferred compounds of formulae IVa and b have $Z^1$ as methyl, tert.butyl, benzyl, trimethylsilylethyl or pentafluorophenyl and $Z^2$ as benzyloxycarbonyl, tert.butyloxycarbonyl or fluoren-9-ylmethoxycarbonyl.

Also part of this invention is a process for the manufacture of particular compounds of formulae Ia or b, which process comprises a) coupling by conventional methods a compound of formula IIa or b in one or, preferably, in more than one step with an amino acid residue or a chain of 2 to 20 amino acid residues wherein reactive moieties in the side chains of the amino acid residue(s) is/are protected or unprotected, and wherein the amino group of the N-terminal amino acid is a free or protected amino group; or b) cyclizing a compound of formula IIIa or b by conventional methods, or c) cleaving off the protecting group(s) from a compound of formula Ia or Ib which contains at least one protecting group by conventional methods to obtain such a compound without protecting groups, or d) converting a compound of formula Ia or b which contains a basic center into a salt using an acid or a compound of formula Ia or Ib which contains an acidic center into a salt using a base by known methods.

The term "lower alkyl" embraces straight-chain or branched saturated hydrocarbon residues with up to 7, preferably up to 4, carbon atoms such as methyl, ethyl, n-propyl, isopropyl, n-butyl, isobutyl, tert.butyl and the like. In an analogous manner, the terms "lower alkenyl" and "lower alkynyl" embrace unsaturated hydrocarbon residues with up to 7, preferably up to 4, carbon atoms which contain a double bond or, respectively, a triple bond, such as vinyl, ethynyl, allyl, propargyl and the like. The term "lower alkoxy" embraces alkyloxy groups in the sense of the above definition of the term "lower alkyl". The term "aryl" embraces phenyl residues optionally mono- or disubstituted by lower alkyl or lower alkoxy or substituted by lower alkylenedioxy. The term "aryloxy" embraces aryl residues as defined above which are linked via an oxygen bridge. Similarly, the term "lower aralkoxy" embraces lower alkoxy residues substituted by an aryl residue as defined above. The term "halogen" denotes the four atoms fluorine, chlorine, bromine and iodine unless expressly indicated to the contrary.

Any known amino acid residues may be used in the compounds of this invention. As amino acid residues there primarily come into consideration those which are derived from x-amino acids, especially from natural α-amino acids; the amino acid residues can, insofar as their α-C atom is asymmetric, be present not only in the L form, but also in the D form, and they can be optionally protected by which is meant protecting reactive moieties with known protecting groups suitable to the specific residue, or left unprotected. Hereinafter there is given a list of amino acids which, or the residues of which, are particularly suitable for the purpose of the present invention, with the abbreviations corresponding to the relevant IUPAC Rules (Biochemistry 11, 726 (1972)) and to generally usual practice.

| | |
|---|---|
| $Ac_3c$ | 1-Aminocyclopropanecarboxylic acid |
| $Ac_4c$ | 1-Aminocyclobutanecarboxylic acid |
| $Ac_5c$ | 1-Aminocyclopentanecarboxylic acid |
| $Ac_6c$ | 1-Aminocyclohexanecarboxylic acid |
| $Ac_7c$ | 1-Aminocycloheptanecarboxylic acid |
| Aib | 2-Amino-2-methylpropionic acid |
| Ala | L-Alanine |

| | |
|---|---|
| D-Ala | D-Alanine |
| β-Ala | β-Alanine |
| Arg | L-Arginine |
| D-Arg | D-Arginine |
| Asn | L-Asparagine |
| D-Asn | D-Asparagine |
| Asp | L-Aspartic acid |
| D-Asp | D-Aspartic acid |
| D-Asp (ONa) | Sodium D-aspartate |
| $C_3$al | L-3-Cyclopropylalanine |
| $C_4$al | L-3-Cyclobutylalanine |
| $C_5$al | L-3-Cyclopentylalanine |
| $C_6$al | L-3-Cyclohexylalanine |
| Cys | L-Cysteine |
| D-Cys | D-Cysteine |
| Glu | L-Glutamic acid |
| D-Glu | D-Glutamic acid |
| Gln | L-Glutamine |
| D-Gln | D-Glutamine |
| Gly | Glycine |
| His | L-Histidine |
| D-His | D-Histidine |
| Hyp | 4-Hydroxy-L-proline |
| Ile | L-Isoleucine |
| aIle | L-Alloisoleucine |
| D-Ile | D-Isoleucine |
| D-aIle | D-Alloisoleucine |
| D-Itg | D-2-(Isothiazolyl)glycine |
| Leu | L-Leucine |
| D-Leu | D-Leucine |
| tert.-Leu | L-2-Amino-3,3-dimethylbutyric acid |
| D-tert.-Leu | D-2-Amino-3,3-dimethylbutyric acid |
| Lys | L-Lysine |
| D-Lys | D-Lysine |
| Lys (CHO) | $N^6$-Formyl-L-lysine |
| MeAla | N-Methyl-L-alanine |
| MeLeu | N-Methyl-L-leucine |
| MeMet | N-Methyl-L-methionine |
| Met | L-Methionine |
| D-Met | D-Methionine |
| Met(O) | L-Methionine sulphoxide |
| D-Met(O) | D-Methionine sulphoxide |
| Met($O_2$) | L-Methionine sulphone |
| D-Met($O_2$) | D-Methionine sulphone |
| Nal | L-3-(1-Naphthylalanine) |
| D-Nal | D-3-(1-Naphthylalanine) |
| Nle | L-Norleucine |
| D-Nle | D-Norleucine |
| Nva | L-Norvaline |
| D-Nva | D-Norvaline |
| Orn | L-Ornithine |
| D-Orn | D-Ornithine |
| Orn(CHO) | $N^5$-Formyl-L-ornithine |
| Phe | L-Phenylalanine |
| D-Phe | D-Phenylalanine |
| L-Phg | L-Phenylglycine |
| D-Phg | D-Phenylglycine |
| Pip | L-Pipecolic acid |
| D-Pip | D-Pipecolic acid |
| Pro | L-Proline |
| D-Pro | D-Proline |
| Sar | Sarcosine |
| Ser | L-Serine |
| D-Ser | D-Serine |
| Thr | L-Threonine |
| D-Thr | D-Threonine |
| Thz | L-Thiazolidine-4-carboxylic acid |
| D-Thz | D-Thiazolidine-4-carboxylic acid |
| Trp | L-Tryptophane |
| D-Trp | D-Tryptophane |
| D-Trp(CHO) | $N^{in}$-Formyl-D-tryptophane |
| D-Trp(O) | D-3-(2,3-Dihydro-2-oxoindol-3-yl)alanine |
| Tyr | L-Tyrosine |
| D-Tyr | D-Tyrosine |
| Tza | L-3-(2-Thiazolyl)alanine |
| D-Tza | D-3-(2-Thiazolyl)alanine |
| Tzg | L-2-(Thiazolyl)glycine |
| D-Tzg | D-2-(Thiazolyl)glycine |
| Val | L-Valine |
| D-Val | D-Valine |

Although any conventional protecting groups may be used, especially suitable protecting groups for amino acids and, respectively, their residues are, for example, for the amino group (as is present e.g. also in the side-chain of lysine)

| | |
|---|---|
| Z | Benzyloxycarbonyl |
| Boc | tert.-Butyloxycarbonyl |
| Fmoc | Fluoren-9-ylmethoxycarbonyl |
| Alloc | Allyloxycarbonyl |
| Teoc | Trimethylsilylethoxycarbonyl |
| Tcc | Trichloroethoxycarbonyl |
| Nps | o-Nitrophenylsulphenyl |
| | p-Bromobenzoyl; | for the carboxyl group (as is present e.g. also in the side-chain of aspartic acid and glutamic acid) by conversion into corresponding esters with the alcohol components

| | |
|---|---|
| tBu | tert.-Butyl |
| Bzl | Benzyl |
| Me | Methyl |
| Ph | Phenyl |
| Pac | Phenacyl |
| | Allyl |
| | Trimethylsilylethyl |
| | Trichloroethyl; | for the guanidine group (as is present, for example, in the side-chain of arginine)

| | |
|---|---|
| Pmc | 2,2,5,7,8-Pentamethylchromane-6-sulphonyl |
| Ts | Tosyl |
| Z | Benzyloxycarbonyl; | for the hydroxy group (as is present, for example, in the side-chain of threonine and serine)

| | |
|---|---|
| tBu | tert.-Butyl |
| Bzl | Benzyl |
| | Trityl; | and for the mercapto group (as is present, for example, in the side-chain of cysteine)

| | |
|---|---|
| Bu | tert.-Butyl |
| Bzl | Benzyl |
| | Trityl |
| | 2-Methoxytrityl. |

When $R^1$ signifies aryl as defined above, preferred is a phenyl residue mono- or disubstituted by lower alkyl or lower alkoxy or a phenyl residue substituted by lower alkylenedioxy. $R^2$ conveniently contains 9 to 15 amino acid residues, especially 9, 12 or 15 amino acid residues. Residues of α-amino acids in which the α-C atom, when it is asymmetric, is preferably present in the L configuration primarily come into consideration. For example, the amino acid residues present in $R^2$ can be derived from L-alanine, L-glutamine, L-glutamic acid, L-isoleucine, L-leucine, L-lysine or 2-amino-2-methylpropionic acid. When the amino group of the N-terminal amino acid in the residue $R^2$ is protected as defined above, then the protecting group can be, for example, an acyl group such as p-bromobenzoyl. Conveniently, $A^1$ or $A^3$ signifies a residue of L- or, respectively, D-alanine, asparagine, aspartic acid, glutamine, glutamic acid or lysine or of 2-amino-2-methylpropionic acid and $A^2$ or $A^4$ signifies a residue of L- or, respectively, D-alanine, asparagine, aspartic acid, glutamine, glutamic acid or lysine. Preferably, $A^1$ or $A^3$ signifies L- or, respectively, D-alanyl and $A^2$ or $A^4$ signifies L- or, respectively, D-alanyl.

When the benzene, furan, thiophene, pyridine or pyrimidine ring denoted by Z is substituted, then it is conveniently mono- or disubstituted by nitro, amino, lower alkanoylamino, hydroxy, lower alkoxy, lower alkanoyloxy, lower alkyl, fluorine, cyano, carboxy or formyl or is condensed with a benzene ring to form a bicyclic system.

Preferably, Y signifies a residue of formula (a) in which n signifies the number 0 and Z and the two C atoms together signify a benzene ring.

The compounds of formulae Ia and Ib as well as their salts can be manufactured in accordance with the invention by using known methods to do the following:

coupling a compound of the general formula

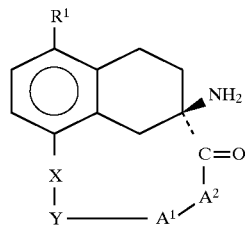

IIa or

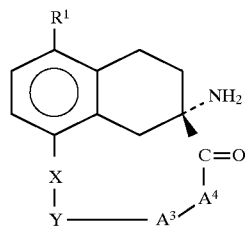

IIb wherein $R^1$, $A^1$, $A^2$, $A^3$, $A^4$, X and Y are as defined above, in one step or, preferably, in stages with an optionally protected chain of up to 20 amino acids, the N-terminal amino acid of which has a free or protected amino group; or b) cyclizing a compound of the general formula

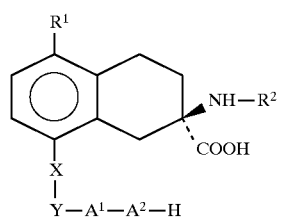

IIIa or

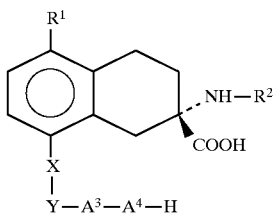

IIIb wherein $R^1$, $R^2$, $A^1$, $A^2$, $A^3$, $A^4$, X and Y are as defined above; or c) cleaving off the protecting group(s) from a compound of formula Ia or Ib which contains at least one protecting group; or d) converting a compound of formula Ia or Ib which contains a basic centre or an acidic centre into a salt using an acid or, respectively, a base.

In accordance with process variant a), the free amino group of a compound of formula IIa or IIb is coupled with a peptide component having a C-terminal free carboxyl group, and in the case of the cyclization of a compound of formula IIIa or IIIb a free carboxyl group and a free amino group are coupled with one another with the formation of an amide bond.

Methods which are generally used in peptide chemistry and which will be familiar to any person skilled in the art are used for carrying out these process variants. Solid phase synthesis methods can also be used; polystyrene-divinylbenzene and the like is, for example, suitable as the carrier.

In process variant a) coupling is conveniently carried out in a first stage with a single amino acid and the remainder of the desired chain is introduced in a second stage.

All possible activating re agents which are conventional in peptide chemistry can be used to carry out the coupling according to process variants a) and b), such as e.g. O-benzotriazol-1-yl-N,N,N',N'-tetramethyl-uronium hexafluorophosphate (HBTU); O-(1,2-dihydro-2-oxo-1-pyridyl)-N,N,N',N'-tetramethyl-uronium tetrafluoroborate (TPTU); 2-( H-benzotriazol-1-yl)-1,1,3,3-tetramethyluronium tetrafluoroborate (TBTU); 1,1,3,3-tetramethyl-2-[1H-1,2,3-triazolo[5,4-b]pyridin-1-yl]-uronium tetrafluoroborate (TATU); 1-hydroxybenzotriazole (HOBT) or 3H-1,2,3-triazolo[5,4-b]pyridin-1-ol (HOAT) in combination with N,N-dicyclohexylcarbodiimide and the like.

By cleaving off the protecting group(s) from a compound of formula Ia or Ib obtained which contains at least one protecting group there is obtained in accordance with process variant c) a corresponding compound of formula Ia or Ib which does not contain protecting group(s). The cleavage of the protecting group(s) is effected according to methods which are conventional in peptide chemistry and which will be familiar to any person skilled in the art, of course while taking into consideration the nature of the protecting group (s) to be removed. Thus, the protecting groups referred to above can be cleaved off, for example, as follows:

Z: Catalytic hydrogenation in the presence of Pd/C in a lower alkanol such as methanol or ethanol.

Boc: Using trifluoroacetic acid/methylene chloride (1:1) or using saturated hydrogen chloride solution in ethyl acetate.

Fmoc: Using piperidine or 1,8-diazabicyclo[5.4.0]-undec-7-ene in dimethylformamide.

Alloc: Using palladium-tetrakis-triphenylphosphine in tetrahydrofuran/dimethyl sulphoxide/0.1N hydrochloric acid.

Teoc: Using caesium fluoride or tetrabutylammonium fluoride in dimethylformamide or the like.

Tcc: Using zinc in glacial acetic acid or methanol.

Nps: Using sodium rhodanide or potassium rhodanide in a slightly acidic medium.

$^t$Bu: Using trifluoroacetic acid/methylene chloride (1:1).

Bzl: By catalytic hydrogenation in the presence of Pd/C in a lower alkanol such as methanol or ethanol.

Me: Using lithium hydroxide in tetrahydrofuran/methanol/water (3:1:1).

Ph: Using sodium peroxide at pH 10.5.

Pac: Using zinc in glacial acetic acid or methanol or using sodium thiophenolate in dimethylformamide.

Allyl: Using palladium-bis-triphenylphosphine dichloride and tributyltin hydride or using palladium-tetrakis-triphenylphosphine in tetra-hydrofuran/dimethyl sulphoxide/0.5N hydrochloric acid.

Trimethylsilylethyl: Using caesium fluoride or tetrabutylammonium fluoride in dimethylformamide or the like.

Trichloroethyl: Using zinc in glacial acetic acid or methanol.

Pmc: Using aqueous trifluoroacetic acid.

Ts: Using sodium in liquid ammonia or liquid hydrogen fluoride.

In an analogous manner, a compound of formula Ia or Ib manufactured by solid phase synthesis on a polystyrene-divinyl benzene resin or the like can be cleaved off from the carrier resin, for example using "Field's reagent", i.e. a mixture of 82.5% trifluoroacetic acid, 5% phenol, 5% water, 5% thioanisole and 2.5% 1,2-ethanedithiol.

In accordance with process variant d), a compound of formula Ia or Ib which contains a basic center or an acidic center can be converted into a salt using an acid or, respectively, a base, which can be effected according to conventional methods which will be familiar to any person skilled in the art. Acids which can be used here are inorganic acids such as hydrochloric acid, sulphuric acid, phosphoric acid or the like or organic acids such as trifluoroacetic acid, methanesulphonic acid, p-toluenesulphonic acid or the like and bases which can be used are inorganic bases such as potassium hydroxide, sodium hydroxide or the like or organic bases such as triethylamine, dimethylaminopyridine or the like.

The starting materials of formula IIa or IIb and IIIa or IIIb required for process variants a) and b) can be prepared from compounds of the general formulae

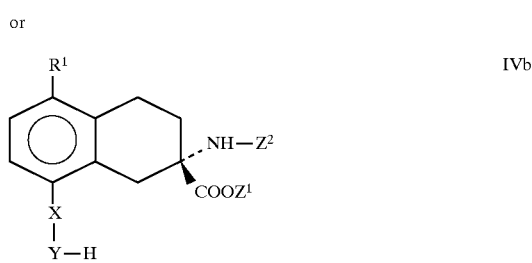

wherein $R^1$, X and Y are as defined above, and $Z^1$ signifies a carboxyl protecting group and $Z^2$ signifies an amino protecting group, both as defined above. In particular, $Z^1$ signifies methyl, tert.-butyl, benzyl, trimethylsilylethyl or pentafluorophenyl and $Z^2$ signifies benzyloxycarbonyl, tert.-butyloxycarbonyl or 9-fluorenylmethoxycarbonyl. In the compounds of formulae IVa or b, $Z^1$ and $Z^2$ may be selected to provide any combination of these groups.

The preparation of the compounds of formulae IVa and IVb and their conversion into compounds of formula IIa or IIb and IIIa or IIIb are illustrated in more detail hereinafter, in part on the basis of Reaction Schemes. With the guidance provided in the Reaction Schemes and subsequent discussion, a skilled person can use known techniques and reagents to obtain compounds which may be converted into compounds of this invention using schemes herein provided. Thus, the steps in the Reaction Schemes are performed using conventional methods, conditions, and reagents which would be known to a skilled person. Initial starting materials and reagents are conventional and may be obtained from known sources such as clinical suppliers, or synthesized by known methods.

Reaction Scheme 1

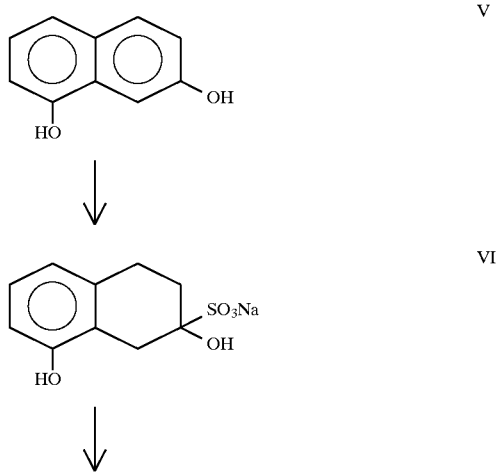

13
-continued
Reaction Scheme 1
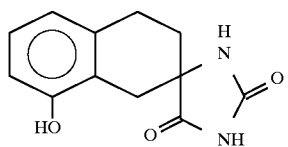 VII
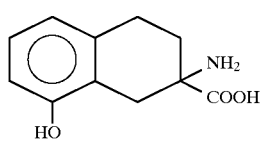
14
-continued
Reaction Scheme 1
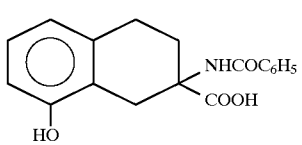 IX
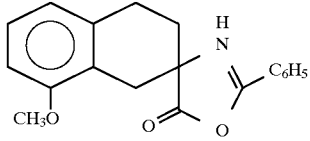 VIII
Reaction Scheme 2
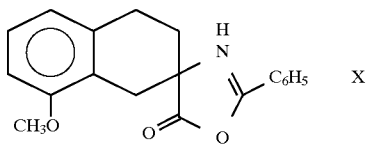 X
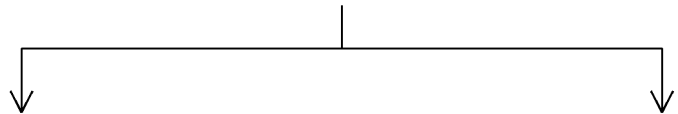
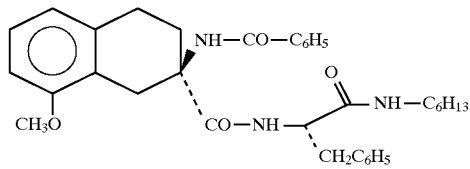
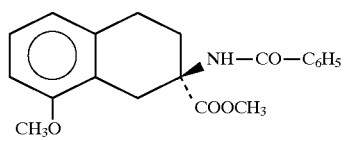 XIIa
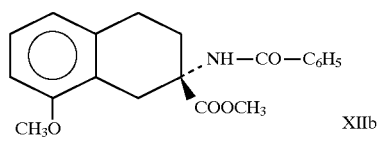 XIIb

-continued
Reaction Scheme 2

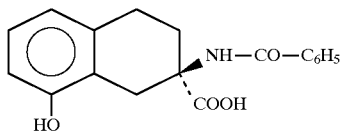 XIIIa

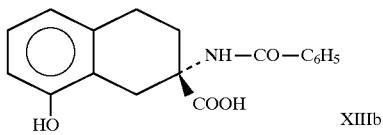 XIIIb

V→VI

1,7-Dihydroxynaphthalene (V), a known compound can be converted by means of lithium in liquid ammonia/tetrahydrofuran/tert.-butanol into 8-hydroxy-1,2,3,4-tetrahydronaphthalen-2-one, which can be converted—without the necessity of isolation—by means of sodium hydrogen sulphite into sodium (rac)-2,8-dihydroxy-1,2,3,4-tetrahydronaphthalene-2-sulphonate (VI).

VI→VII

The sodium salt of formula VI can be converted into the racemic spiro compound of formula VII by means of potassium cyanide and ammonium carbonate in ethanol/water.

VII→VIII

The Spiro compound of formula VII can be converted into (rac)-2-amino-8-hydroxy-1,2,3,4-tetrahydrohaphthalene-2-carboxylic acid (VIII) by heating with barium hydroxide in water and subsequent acidification, e.g. with aqueous sulphuric acid.

VIII→IX

The compound of formula VIII is firstly acylated by means of benzoyl chloride or the like, conveniently in the presence of an acid-binding agent such as sodium hydroxide or the like. By treating the acylation product with sodium hydroxide in dioxan there can be obtained (rac)-2-benzamido-8-hydroxy-1,2,3,4-tetrahydronaphthalene-2-carboxylic acid.

IX→X

By treating the compound of formula IX with dicyclohexyl-carbodiimide in dichloromethane or the like and subsequent methylation, conveniently by means of dimethyl sulphate in the presence of a strong base such as sodium hydride in dioxan or the like, there can be obtained (rac)-3,4-dihydro-8-methoxy-2-phenylspiro[naphthalen-2(1H),4'(5'H)-oxazol]-5'-one.

X→XIa and XIb

The compound of formula X can be converted by means of L-phenylalanine cyclohexylamide into a mixture of the two diastereoisomeric compounds of formulae XIa and XIb, which can be separated by crystallization into its components XIa and XIb.

XIa→XIIa and XIb→XIIb

By treating the compound of formula XIa or XIb with trifluoromethanesulphonic acid there is obtained L-phenylalanine cyclohexylamide trifluoromethanesulphonate and the compound of formula XIIa or XIIb.

XIIa→XIIIa and XIIb→XIIIb

By treating the compound of formula XIIa or XIIb with boron tribromide in dichloromethane or the like there is obtained the compound of formula XIIIa or XIIIb.

Various transformations, which are illustrated in Reaction Scheme 3 hereinafter, are possible starting from the compound of formula XIIIa; the same transformations are, of course, also possible starting from the compound of formula XIIIb.

Reaction Scheme 3

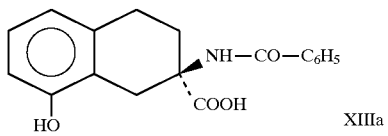 XIIIa

-continued
Reaction Scheme 3

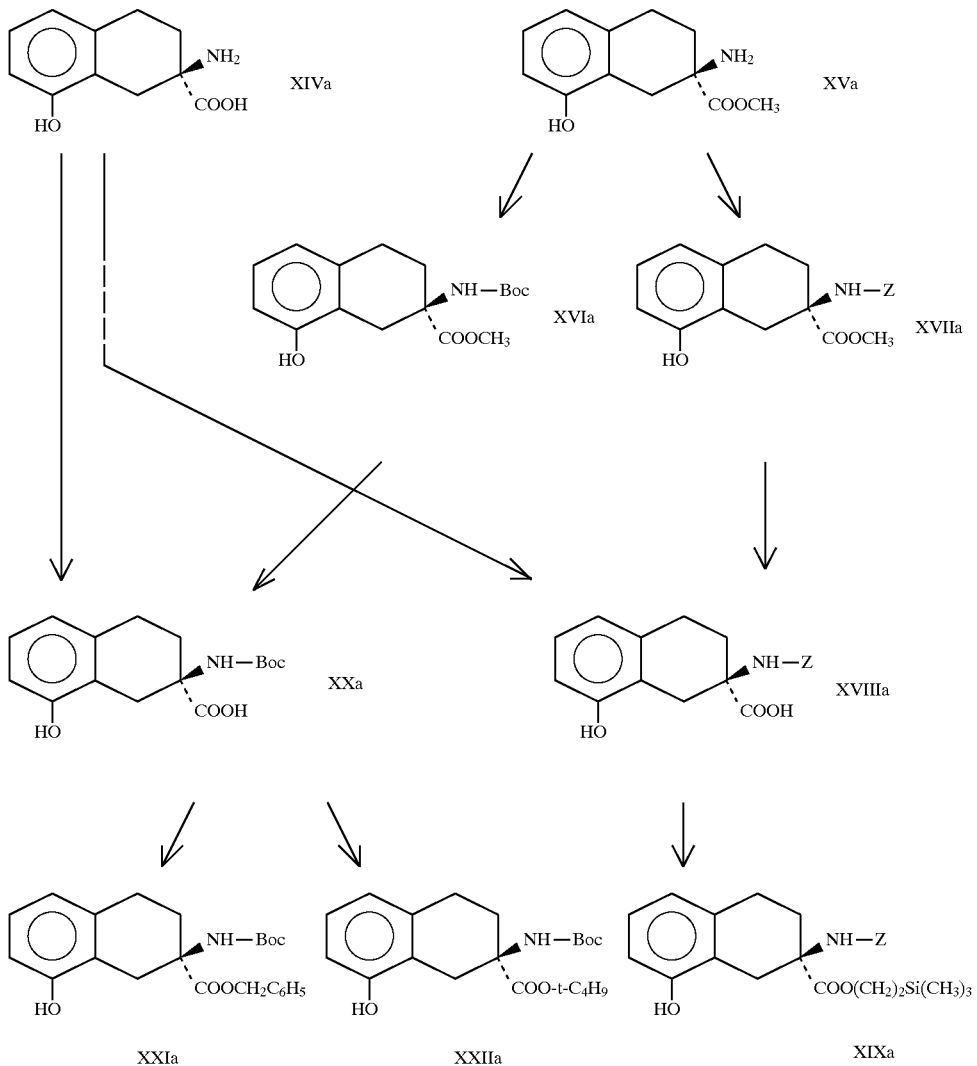

Z signifies benzyloxycarbonyl
Boc signifies tert.-butyloxcarbonyl

The various transformations according to Reaction Scheme 3 are carried out according to methods which are known per se and which will be familiar to any person skilled in the art, conveniently by means of the reagents referred to hereinafter.

XIIa→XIVa

5% hydrochloric acid in dioxan at 100° (bomb tube).

XIIIa→XVa

25% hydrochloric acid in dioxan at 100° (bomb tube), then oxalyl chloride in methanolic hydrochloric acid.

XVa→XVIa

Di-tert.-butyl dicarbonate in dimethylformamide.

XVa→XVIIa

N-(Benzyloxycarbonyloxy)-succinimide and sodium hydrogen carbonate in dioxan.

XVIIa→XVIIIa

Lithium hydroxide in tetrahydrofuran/methanol/water.

XIVa→XVIIIa

N-(Benzyloxycarbonyloxy)-succinimide and sodium hydrogen carbonate in dioxan.

XVIIIa→XIXa

Trimethylsilylethanol/N-ethyl-N'-(3-dimethylaminopropyl)-carbodiimide hydrochloride/1-N-hydroxybenzotriazole/ethyl-diisopropylamine/N,N-dimethylaminopyridine in dimethylformamide.

XIVa→XXa

Di-tert.-butyl dicarbonate/trimethylchlorosilane/ethyl-diisopropylamine in dichloromethane.

XVIa→XXa

Lithium hydroxide in tetrahydrofuran/methanol/water.

XXa→XXIa

Benzyl bromide/1,8-diazabicyclo[5.4.0]undec-7-ene in dimethylformamide or phenyldiazomethane in dichloromethane.

XXa→XXIIa

N,N-Dimethylformamide di-tert.-butyl acetal in toluene.

Compounds of type XVIa, XVIIa, XIXa, XXIa and XXIIa can be brominated in the 5-position, conveniently by means of N-bromosuccinimide in trifluoroethanol, and subsequently already at this stage certain additional variations (as described in more detail below) in the 5-position of the tetrahydronaphthalene structure are possible (see the different meanings of $R^1$ in formulae Ia and Ib), whereby the phenolic hydroxyl group must be temporarily protected in certain instances. Furthermore, the phenolic hydroxyl group in compounds of type XVIa, XVIIa, XIXa, XXIa and XXIIa or in corresponding 5-bromo compounds or in transformation products thereof having other substituents in the 5-position can be replaced by a SH group, for example according to one of the following methods:

a) Reaction with N,N-diethyl-thiocarbamoyl chloride followed by heating and then alkaline hydrolysis, see M. S.

Newman, H. A. Karnes, J. Org. Chem. 31, 3980 (1966);

b) Treatment with trifluoromethanesulphonic anhydride in pyridine; then reaction of the resulting trifluoromethanesulphonate with thiourea in the presence of a nickel catalyst followed by treatment with alkali and then with acid, see K. Takagi, Chem. Lett. 1985, 1307.

Compounds of formulae IVa and IVb can be obtained as follows starting from compounds of type XVIa, XVIIa, XIXa, XXIa and XXIIa or from transformation products thereof, as previously described, or from corresponding compounds prepared, however, from compound XIIIb:

Compounds of formula IVa or IVb in which Y signifies a residue of formula (a) are obtained by reaction with corresponding o-nitro-haloaromatics or corresponding haloaromatics which are substituted in the opposition by protected aminomethyl, such as 2-iodo-nitrobenzene, 2-chloro-3-nitropyridine or the like or, respectively, benzyl N-2-bromobenzylcarbamate or the like, and subsequent reduction of the nitro group or, respectively, cleavage of the protecting group.

Compounds of formula IVa or IVb in which Y signifies a residue of formula (b) are obtained by reaction with a corresponding alkyl halide which is substituted in the 3-position by protected hydroxy, such as 1-bromo-3-tert.butyldimethylsilyloxy-2-methylpropane, cleavage of the O-protecting group, replacement of the hydroxy group by a leaving group such as tosyloxy, replacement of the leaving group by an azido group, e.g. by means of sodium azide, and reduction of the azido group to the amino group, conveniently by catalytic hydrogenation, e.g. in the presence of a palladium catalyst such as Pd-C. When a lower alkanol such as ethanol is used as the solvent in the aforementioned hydrogenation there can be obtained under certain circumstances not only the amino compound, but also the corresponding lower-alkylamino compound (e.g. the corresponding ethylamino compound); the separation of such a mixture can be effected at this stage or at a later stage.

Various transformations are possible in the compounds of formulae IVa and IVb obtained, with the amino group being previously protected as necessary and being subsequently liberated.

On the one hand, variations with respect to the protecting groups can be carried out. Thus, e.g., a tert.-butoxycarbonylamino group can be converted into a fluorenylmethoxycarbonylamino group, a tert.-butyl ester can be converted into a pentafluorophenyl ester or a benzyl ester can be converted into a pentafluorophenyl ester, which can be effected according to methods which are conventional and which will be familiar to any person skilled in the art.

On the other hand, variations with respect to the 5-position of the tetrahydronaphthalene structure are conveniently carried out at this stage; the introduction of bromine is, however, conveniently effected already at an earlier stage, namely at the stage of the compounds of type XVIa, XVIIa, XIXa, XXIa and XXIIa. Thus, compounds of formula IVa and IVb in which $R^1$ signifies bromine can be transformed, for example, as follows:

a) Reaction with organotin compounds in the presence of a palladium catalyst, see T. N. Mitchell, Synthesis 1992, 803–815; J. K. Stille, Angew. Chem. 98, 504–519 (1986); D. R. McKean, G. Parinello, A. F. Renaldo, J. K. Stille, J. Org. Chem. 52, 422 (1987). For example, by means of 3,4-dimethoxyphenyl-trimethylstannate in the presence of tetrakis-(triphenylphosphine)-palladium in dioxan there is obtained a compound of formula IVa or IVb in which $R^1$ signifies 3,4-dimethoxyphenyl.

b) Reaction with borates in the presence of a palladium catalyst, see X. Wang, V. Sniekus, Tetrahedron Lett. 1991, 4879; B. I. Alo, A. Kandil, P. A. Patil, M. J. Sharp, M. A. Siddiqui, V. Snieders, J. Org. Chem. 56, 3763 (1991); T.Oh-e, N. Miyaura, A. Suzuki, Synlett 1990, 221.

Methods a) and b) are suitable for the introduction of aryl, alkenyl, alkynyl and alkyl residues.

c) Reaction with carbon monoxide and an alcohol in the presence of palladium diacetate or the like and a base, see J. K. Stille, P. K. Wong, J. Org. Chem. 40, 532 (1975); A. Cowell, J. K. Stille, J. Amer. Chem. Soc. 102, 4193 (1980). This method is suitable for the introduction of alkoxycarbonyl groups.

d) Reaction with carbon monoxide and hydrogen in the presence of triethylamine or the like and bis-(triphenylphosphine)palladium dichloride or the like, see A. Schoenberg, R. F. Heck, J. Amer. Chem. Soc. 96, 7761 (1974); H. Yoshida, N. Sugita, K. Kudo, Y. Takezaki, Bull. Chem. Soc. Japan 49, 1681 (1976). This method is suitable for the introduction of the formyl group.

e) Reaction with potassium cyanide in the presence of 1,1'-bis-(diphenylphosphino)-ferrocene and bis-(dibenzylideneacetone)-di-palladium in N,N-dimethylacetamide, see K. Takagi, Y. Sakakibara, Chem. Lett. 1989, 1957. This method is suitable for the introduction of the cyano group.

f) Transformation of the formyl group into an alkenyl group by Wittig reaction.

g) Treatment with tert.-butyllithium and subsequent reaction with suitable electrophiles such as e.g. N-formylpiperidine (yields formyl), chloroformic acid ester (yields alkoxycarbonyl) etc.

h) Ullmann coupling with a phenol in the presence of sodium hydride and copper bromide-dimethyl sulphide complex in pyridine, see D. L. Boger, D. Yohannes, J. Org. Chem. 55, 6000 (1990); D. A. Evans, J. A. Ellmann, J. Amer. Chem. Soc. 111, 1063 (1989). This method is suitable for the introduction of aryloxy groups.

i) Reaction of alcohols, especially primary alcohols, under phase transfer catalysis (e.g. PEG-6000, KOH), see. R. Neumann, Y. Sasson, Tetrahedron 39, 3437 (1983). This method is suitable for the introduction of alkoxy and aralkoxy groups.

k) Transformation of the formyl group into the hydroxy group by means of a modified Bayer-Villiger reaction (sodium percarbonate/trifluoroacetic acid), see G. Olah, Synthesis 1991, 739.

Compounds of formula IIa or IIb can be obtained starting from compounds of formula IVa or IVb by firstly coupling with an amino acid component yielding the residue $A^1$ or $A^3$ and thereupon with an amino acid component yielding the residue $A^2$ or $A^4$, subsequently liberating the carboxyl group protected by $Z^1$, then cyclizing and finally liberating the amino group protected by $Z^2$.

Compounds of formula IIa or IIIb can be obtained starting from compounds of formula IVa or IVb by firstly liberating the amino group protected by $Z^2$, coupling this with a peptide component yielding the residue $R^2$ and then coupling with an amino acid component yielding the residue $A^1$ or $A^3$ and thereupon with an amino acid component yielding the residue $A^2$ or $A^4$.

The preparation of the compounds of formula IIa or IIb and of formula IIIa or IIIb from the compounds of formula IVa or IVb is effected according to methods which are conventional in peptide chemistry and which will be familiar to any person skilled in the art.

If an aspartic acid derivative is used in the course of this synthesis as the amino acid component yielding the residue $A^1$ or $A^3$, then in the resulting compound the carboxyl group of the aspartyl residue can be present not only in free form, but as a member of a five-membered ring which is formed with the nitrogen atom of the amide bond linking $A^1$ or $A^3$ with $A^2$ or $A^4$; this ring can—conveniently only after the conversion into a compound of formula Ia or Ib—be opened, e.g. by means of lithium hydroxide or the like.

The compounds of formulae Ia and Ib contain amino acid sequences (see the residue $R^2$), whereby in the compounds of formula I the conformations of dextrorotating peptidic α-helices (with L-amino acid residues) are stabilized and the conformations of levorotating peptidic α-helices (with D-amino acid residues) are destabilized, whereas in the compounds of formula Ib the conformations of levorotating peptidic α-helices (with D-amino acid residues) are stabilized and the conformations of dextrorotating peptidic α-helices (with L-amino acid esters) are destabilized.

The structural elements in the compounds of formula Ia or Ib corresponding to the compounds of formula IIa or IIb can be perceived as mimetics of an α-helical winding. The stabilization or reproduction of the helicity in compounds of formula Ia or Ib depends on whether on the one hand the i→i+4 hydrogen bridge network [see. L. Pauling, R. B. Corey, H. R. Branson, Proc. Natl. Acad. Sci. 37, 205 (1951)] can form and whether on the other hand the 1-amino-1,2,3,4-tetrahydro-naphthalene-2-carboxylic acid building brick induces inherent α-helical conformations at the asymmetric C atom in the 2-position, see C. Spiegler, Synthesis and conformational studies of peptides containing novel α,α-disubstituted amino acids, Dissertation Universität Zürich, 1993).

Figure 1B:
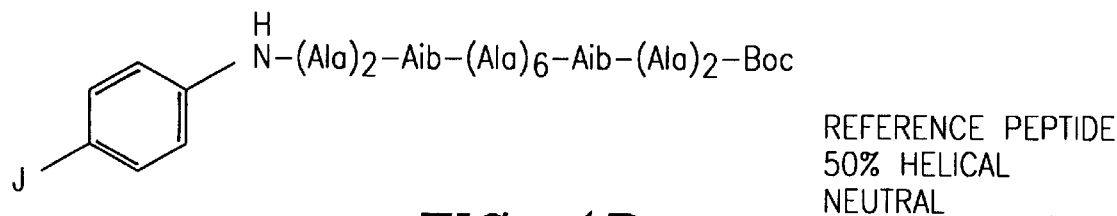
Figure 1C:
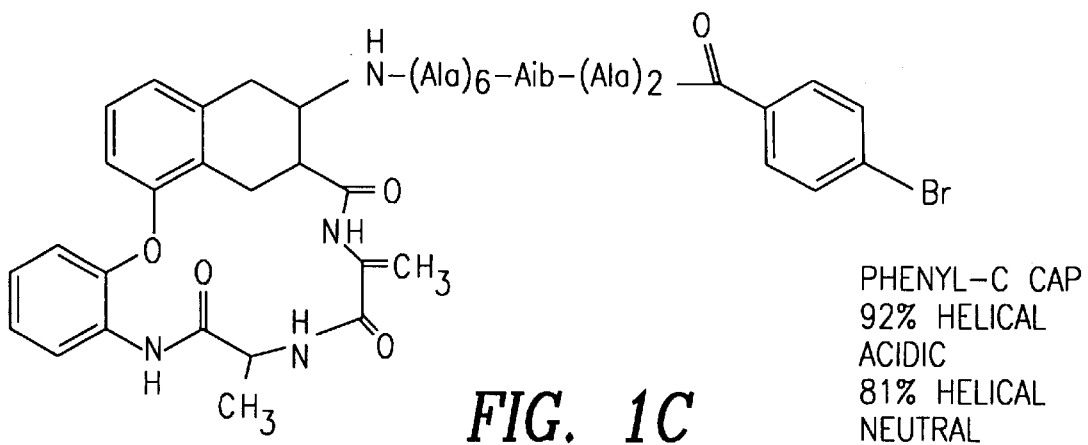

As will be evident from FIG. 1, the helicity determined in trifluoroethanol/water (1:1) of the end product of Example 5.1.3.a is 81% in neutral medium and 92% in acidic medium (HCl), that of a reference peptide of the same length is, however, 50% in neutral and acidic medium [the calculation of the helicity was carried out analogously to Y.-H. Chen, J. T. Wang, H. H. Martinez, Biochemistry 11, 4120 (1972) and Y.-H. Chen, J. T. Wang, K. H. Chau, Biochemistry 13, 3330 (1974)].

The priority of the amino acid residues $A^1$ and $A^2$ or $A^3$ and $A^4$ in the compounds of formula Ia or Ib is somewhat analogous to the compatibility of L- and D-amino acids in peptidic α-helices, see A. Horovitz, J. M. Matthews, A. R. Fersht, J. Mol. Biol. 227, 560–568 (1992).

Having regard to their properties, compounds of formula Ia or Ib are suitable as mimetics of exposed helical domains of proteins in order to clarify their rôle with respect to interactions with other proteins (receptors, enzymes or the like) or with DNA or RNA. In particular, amino acid sequences having biological activity can be determined by means of compounds of formula Ia or Ib. The compounds of formula Ia or Ib are therefore suitable as research tools in order to prepare biologically active peptide sequences. The compounds of formula Ia or Ib are, however, also potentially suitable as medicaments, with the respective therapeutic applicability depending upon their ability as mimetics of the domains of peptides or proteins which can interact with other proteins or with DNA or RNA through α-helical conformation, from which $R^2$ is derived.

In the following Examples, which illustrate the invention in more detail but are not intended to limit its scope in any manner, all temperatures are given in degrees Celsius. The designation of the Examples in which the end products have the R configuration at the asymmetric C-atom in the 2-position of the 2-amino-1,2,3,4-tetrahydro-naphthalene-2-carboxylic acid building brick always ends with "a", that of the Examples in which the end products have the S configuration at the C atom in question invariably ends with "b".

EXAMPLE 1.1

15.0 g of lithium metal pieces were added within 20 minutes under argon and while cooling (dry ice/acetone) analogously to D. W. Johnson, L. N. Mander, Aust. J. Chem. 1974, 27, 1277 to a solution of 120.0 g (750 mmol) of 1,7-dihydroxy-naphthalene in a mixture of 300 ml of tetrahydrofuran, 142 ml of tert.-butyl alcohol and 1000 ml of liquid ammonia. The mixture was stirred for 1 hour and then treated with 400 ml of methanol, whereupon the mixture was stirred at −70° for 1 hour, the ammonia was removed under a $N_2$ stream, the residue was acidified with aqueous 10% HCl and extracted with 3×2.0 l of ethyl acetate. The organic phase was washed twice with 1.0 l of saturated sodium chloride solution, dried over $MgSO_4$ and evaporated. The residue was dissolved in 500 ml of ethyl acetate and 40 ml of ethanol, whereupon the solution was treated with 1.0 l of 38–40% sodium hydrogen sulphite solution and the mixture was shaken for 18 hours. The precipitate was filtered off, washed with dilute $NaHSO_3$ solution and ethyl acetate and dried in a vacuum over Sicapent, 96.2 g (48%) of sodium (rac)-2,8-dihydroxy-1,2,3,4-tetrahydro-naphthalene-2-sulphonate being obtained; m.p. 160°–162°.

EXAMPLE 1.2

A suspension of 48.0 g (180 mmol) of sodium (rac)-2,8-dihydroxy-1,2,3,4-tetrahydro-naphthalene-2-sulphonate, 20.2 g (310 mmol) of potassium cyanide and 118.1 g (1 mol) of ammonium carbonate in 800 ml of ethanol/water (4:1) was stirred at 65° internal temperature for 2 hours, then cooled and poured into a mixture of ice and 1.2 l of 2N aqueous HCl. The suspension was left to stand overnight and then filtered. The residue was washed with $H_2O$ and dried in a vacuum over SICAPENT®, 31.5 g (75.4%) of (rac)-3',4'-dihydroxy-8'-hydroxyspiro[imidazolidine-4,2'(1'H)-naphthalene]-2,5-dione being obtained; m.p. 232°–234° (dec.).

EXAMPLE 1.3

A suspension of 30.0 g (129 mmol) of (rac)-3',4'-dihydroxy-8'-hydroxyspiro[imidazolidine-4',2'(1'H)-naphthalene]-2,5-dione and 203.8 g of $Ba(OH)_2.8H_2O$ in 800 ml of water was stirred at 125° in a steel autoclave for 24 hours, then cooled, acidified with $4N\ H_2SO_4$ solution, whereupon the mixture was heated on a water bath for 1 hour, cooled, filtered and the filter residue was washed with dilute $H_2SO_4$ solution. The acidic filtrate was concentrated to a volume of about 300 ml and neutralized with concentrated aqueous ammonia solution, whereupon a precipitate separated. The suspension was left to stand overnight and was then filtered. The residue was dried in a vacuum over SICAPENT®, 20.5 g (83.1%) of (rac)2-amino-8-hydroxy-1,2,3,4-tetrahydro-naphthalene-2-carboxylic acid being obtained; m.p. >280° (dec.).

EXAMPLE 1.4

50 ml of 2N NaOH and 40.3 ml (345 mmol) of benzoyl chloride were simultaneously added dropwise from 2 dropping funnels to a solution of 19.0 g (99.4 mmol) of (rac)-2-amino-8-hydroxy-1,2,3,4-tetrahydro-naphthalene-2-carboxylic acid in 210 ml of 1N NaOH while cooling with ice and stirring in such a manner that the internal temperature did not rise above 15°. The reaction mixture was subsequently brought slowly to room temperature, stirred for 2 hours, acidified with 2N HCl and extracted twice with 250 ml of ethyl acetate. The combined organic phases were dried over $MgSO_4$ and evaporated. The residue was dissolved in 300 ml of dioxan and the solution was treated with 150 ml of 2N NaOH while cooling with ice. The reaction mixture was stirred overnight, acidified with 4N HCl and extracted three times with 300 ml of ethyl acetate. The combined organic phases were dried over $MgSO_4$ and evaporated. The residue was taken up in 500 ml of diethyl ether/hexane (4:1) and the suspension was stirred overnight and then filtered. The filter residue was dried in a high vacuum, 28.6 g (92.4%) of (rac)-2-benzamido-8-hydroxy-1,2,3,4-tetrahydro-naphthalene-2-carboxylic acid being obtained. M.p. 234°–236° (dec.).

EXAMPLE 1.5

12.53 g (60.7 mmol) of N,N-dicyclohexylcarbodiimide were added portionwise while cooling to a suspension of 18.0 g (57.8 mmol) of (rac)-2-benzamido-8-hydroxy-1,2,3,4-tetrahydro-naphthalene-2-carboxylic acid in 150 ml of dichloromethane. The mixture was stirred at room temperature for 2 hours and then filtered, whereupon the filter residue was washed with dichloro-methane. The filtrate was evaporated and the residue was dried in a high vacuum and dissolved in 150 ml of absolute dioxan. The solution was treated portionwise with 2.80 g of sodium hydride suspension (55%) while cooling with ice and under argon, whereupon the mixture was stirred at room temperature for 30 minutes and then 16.5 ml of dimethyl sulphate were added. The suspension was stirred at 80° for 1 hour, cooled and then poured into a mixture of ice, 10% sodium hydrogen phosphate solution and ethyl acetate. The aqueous phase was extracted with ethyl acetate and the combined organic phases were dried over $MgSO_4$ and concenrated. The residue was chromatographed on 500 g of silica gel with ethyl acetate/hexane (1:4), there being obtained after crystallization from diethyl ether/hexane (1:2) and drying in a high vacuum 13.6 g (76.5%) of (rac)-3,4-dihydro-8-methoxy-2'-phenyl-spiro[naphthalen-2(1H),4'(5'H)-oxazol]-5'-one. M.p. 108°–109°.

EXAMPLE 1.6

A mixture of 12.6 g (41 mmol) of (rac)-3,4-dihydro-8-methoxy-2'-phenyl-spiro[naphthalen-2(1H), 4'(5'H)-oxazol]-5'-one and 15.15 g (61.5 mmol) of L-phenylalanine cyclohexylamide in 120 ml of N-methylpyrrolidone was stirred at 60° for 18 hours, then cooled and subsequently poured into a mixture of 300 ml of water and 500 ml of ethyl acetate. The organic phase was extracted twice with 250 ml of 0.5N HCl and the combined aqueous phases were extracted with ethyl acetate. The combined organic phases were washed with saturated sodium chloride solution, dried over $MgSO_4$ and evaporated. The residue was suspended in 300 ml of ethyl acetate for 2 hours, whereupon the suspension was filtered and the residue was washed with ethyl acetate, recrystallized from ethyl acetate/hexane (6:1) and dried. There were obtained 10.44 g (46%) of $N^2$-[(S)-2-benzamido-8-methoxy-1,2,3,4-tetrahydro-naphthalene-2-carbonyl]L-phenylalanine cyclohexylamide. M.p. 186°–188°. $[\alpha]_D$=+12.0° (c=0.2, methanol).

The filtrate was concentrated and the residue was chromatographed on 1 kg of silica gel with diethyl ether/isopropanol (99.5:0.5), whereupon after recrystallization from ethyl acetate/hexane (1:1) and drying in a high vacuum 10.25 g (45.2%) of $N^2$-[(R)-2-benzamido-8-methoxy-1,2,3,4-tetrahydro-naphthalene-2-carbonyl]-L-phenylalanine cyclohexylamide were obtained. M.p. 191°–192°. $[\alpha]_D$=−21.0° (c=0.2, methanol).

EXAMPLE 1.7.b 7.1 ml (80.74 mmol) of trifluoromethanesulphonic acid were added dropwise under argon and while cooling with ice to a suspension of 7.5 g (13.54 mmol) of $N^2$-[(S)-2-benzamido-8-methoxy-1,2,3,4-tetrahydro-naphthalene-2-carbonyl]-L-phenylalanine cyclohexylamide in 35 ml of methanol. The mixture was stirred at 80° in a bomb tube for 4 hours, then cooled and subsequently concentrated to a volume of ~20 ml. 50 ml of dichloromethane were added while stirring, the suspension was filtered and the filter residue was washed with dichloromethane and dried, 4.48 g (83%) of L-phenylalanine cyclohexylamide trifluoromethanesulphonate being isolated. The filtrate was washed with water, dried over $MgSO_4$ and concentrated. The residue was chromatographed on 350 g of silica gel with ethyl acetate/hexane (2:3), whereupon 4.0 g (87%) of methyl (S)-2-benzamido-8-methoxy-1,2,3,4-tetrahydro-naphthalene-2-carboxylate were obtained. $[\alpha]_D$=+144.0° ($CHCl_3$, c=0.2). IR(KBr): 3366w(br.), 3062w, 2998w, 2948w, 1739s, 1647s, 1586m, 1527s, 1468s, 1437m, 1292m, 1259s, 1099m, 1047m, 774w, 713m. (D. Obrecht, Helv. Chim. Acta 1992, 75, 1666).

EXAMPLE 1.7.a

In analogy to Example 1.7.b, from 8.79 g (15.87 mmol) of $N^2$-[(R)-2-benzamido-8-methoxy-1,2,3,4-tetrahydro-naphthalene-2-carbonyl]-L-phenylalanine cyclohexylamide there were obtained 4.78 g (88%) of methyl (R)-2-benzamido-8-methoxy-1,2,3,4-tetrahydro-naphthalene-2-carboxylate. $[\alpha]_D$=−142.5° (c=0.2, $CHCl_3$).

EXAMPLE 1.8.b 28.7 ml of boron tribromide solution (1M in dichloromethane) were added dropwise under argon and while cooling with ice to a solution of 1.95 g (5.75 mmol) of methyl (S)-2-benzamido-8-methoxy-1,2,3,4-tetrahydro-naphthalene-2-carboxylate in 15 ml of dichloromethane. The reaction mixture was stirred at 0° for 30 minutes and at room temperature for 3 hours and then poured into a mixture of ice, saturated ammonium chloride solution and ethyl acetate. The organic phase was separated, extracted with saturated sodium chloride solution, dried over $MgSO_4$ and concentrated. The residue was dried in a high vacuum, suspended in diethyl ether/hexane (1:4) and filtered off. The filter residue was dried, there being obtained 1.75 g (97.8%) of (S)-2-benzamido-8-hydroxy-1,2,3,4-tetrahydro-naphthalene-2-carboxylic acid. $[\alpha]_D$=+84.3° (c=0.3, methanol). IR(KBr): 3362m(br.), 3064w, 3022w, 2976w, 2938w, 2620w, 1718s, 1644s, 1588m, 1523s, 1487m, 1467s, 1330m, 1278s, 1082w, 716m.

EXAMPLE 1.8.a

In analogy to Example 1.8.b, from 2.71 g (7.98 mmol) of methyl (R)-2-benzamido-8-methoxy-1,2,3,4-tetrahydro-naphthalene-2-carboxylate there were obtained 2.42 g (97.4%) of (R)-2-benzamido-8-hydroxy-1,2,3,4-tetrahydro-naphthalene-2-carboxylic acid. $[\alpha]_D=-85.7°$ (c=0.3, methanol).

EXAMPLE 2.1.b

A solution of 1.75 g (5.62 mmol) of (S)-2-benzamido-8-hydroxy-1,2,3,4-tetrahydro-naphthalene-2-carboxylic acid in 12 ml of 25% hydrochloric acid and 6 ml of dioxan was heated to 110° in a bomb tube for 8 hours, then cooled and subsequently evaporated to dryness. The residue was dried overnight in a high vacuum over Sicapent and then suspended in 20 ml of diethyl ether while stirring, whereupon the suspension was filtered. The filter residue was washed with diethyl ether and dried in a high vacuum and then dissolved in 3 ml of methanol and 3 ml of 15% methanolic hydrochloric acid. The solution was treated with 0.42 ml (3.89 mmol) of oxalyl chloride under argon and while cooling with ice, whereupon the mixture was stirred at 50° in a bomb tube for 20 hours, then cooled and subsequently poured into a mixture of saturated sodium hydrogen carbonate solution and chloroform. The aqueous phase was extracted with chloroform/methanol (6:1). The combined organic phases were dried over MgSO$_4$, filtered and concentrated. The residue was chromatographed on 150 g of silica gel with chloroform/methanol (6:1), there being obtained after recrystallization from ethyl acetate/hexane 1.05 g (84.4%) of methyl (S)-2-amino-8-hydroxy-1,2,3,4-tetrahydro-naphthalene-2-carboxylate. M.p. 183°–185°. $[\alpha]_D=-22.7°$ (c=0.15, methanol).

EXAMPLE 2.1.a

In analogy to Example 2.1.b, from 2.40 g (7.71 mmol) of (R)-2-benzamido-8-hydroxy-1,2,3,4-tetrahydro-naphthalene-2-carboxylic acid there were obtained 1.60 g (95.3%) of methyl (R)-2-amino-8-hydroxy-1,2,3,4-tetrahydro-naphthalene-2-carboxylate. M.p. 184°–185°.

EXAMPLE 2.2.b

A suspension of 9.2 g (29.55 mmol) of (S)-2-benzamido-8-hydroxy-1,2,3,4-tetrahydro-naphthalene-2-carboxylic acid in 45 ml of dioxan and 62 ml of 25% hydrochloric acid was heated to 100° in a bomb tube for 24 hours, then cooled, concentrated to half of the volume and extracted with ethyl acetate. The organic phase was washed with water, whereupon the combined aqueous phases were reduced to a volume of 200 ml and adjusted to pH 7 with concentrated ammonia solution. The solution obtained was filtered over MCI gel (CHP20P; 75–150μ) (water, water/methanol (95:5) →water/methanol (9:1)), whereupon after drying over SICAPENT® 5.30 g (86.6%) of (S)-2-amino-8-hydroxy-1,2,3,4-tetrahydro-naphthalene-2-carboxylic acid were obtained. M.p. >270° (dec.). $[\alpha]_D=+7.0°$ (c=0.2, 0.1N HCl).

EXAMPLE 2.2.a

In analogy to Example 2.2.b, from 4.50 g (14.45 mmol) of (R)-2-benzamido-8-hydroxy-1,2,3,4-tetrahydro-naphthalene-2-carboxylic acid there were obtained 2.49 g (83%) of (R)-2-amino-8-hydroxy-1,2,3,4-tetrahydro-naphthalene-2-carboxylic acid. M.p. >272° (dec.). $[\alpha]_D=-5.0°$ (c=0.2, 0.1N HCl).

EXAMPLE 2.3.b

A solution of 924 mg (4.24 mmol) of di-tert.-butyl dicarbonate in 1.5 ml of DMF was added while cooling with ice and under argon to a solution of 780 mg (3.53 mmol) of methyl (S)-2-amino-8-hydroxy-1,2,3,4-tetrahydro-naphthalene-2-carboxylate in 10 ml of DMF. The reaction mixture was stirred at 0° for 30 minutes and at room temperature for 18 hours and then poured into a mixture of water and ethyl acetate. The organic phase was separated, extracted with water, dried over MgSO$_4$ and concentrated. The residue was chromatographed on 100 g of silica gel with ethyl acetate/hexane (1:2), whereupon after recrystallization from diethyl ether/hexane and drying 1.0 g (88.1%) of methyl (S)-2-(tert.butoxycarbonylamino)-8-hydroxy-1,2,3,4-tetrahydro-naphthalene-2-carboxylate was obtained. M.p. 186°–187°. $[\alpha]_D=+95.0°$ (C=0.2, chloroform).

EXAMPLE 2.3.a

In analogy to Example 2.3.b, from 1.46 g (6.60 mmol) of methyl (R)-2-amino-8-hydroxy-1,2,3,4-tetrahydro-naphthalene-2-carboxylate there were obtained 1.80 g (85%) of methyl (R)-2-(tert.butoxycarbonylamino)-8-hydroxy-1,2,3,4-tetrahydro-naphthalene-2-carboxylate. M.p. 186°–187°. $[\alpha]_D=-93.5°$ (c=0.2, chloroform).

EXAMPLE 2.4.b

A suspension of 1.1 g (4.27 mmol) of methyl (S)-2-amino-8-hydroxy-1,2,3,4-tetrahydro-naphthalene-2-carboxylate in 22 ml of dioxan was treated at room temperature with 2.12 g (8.54 mmol) of N-(benzyloxycarbonyloxy)-succinimide and 717 mg (8.54 mmol) of sodium hydrogen carbonate. The reaction mixture was stirred at room temperature for 4 hours and then poured into a mixture of saturated sodium chloride solution and ethyl acetate. The organic phase was separated, dried over MgSO$_4$ and concentrated. The residue was chromatographed on 200 g of silica gel with chloroform/methanol (98:2→95:5), whereupon after drying 1.30 g (86.9%) of methyl (S)-2-benzyloxycarbonylamino-8-hydroxy-1,2,3,4-tetrahydro-naphthalene-2-carboxylate were obtained. M.p. 58°–68° (sintering). $[\alpha]_D=+85.0°$ (c=0.2, chloroform).

EXAMPLE 2.5.b

A solution of 800 mg (2.26 mmol) of methyl (S)-2-benzyloxycarbonylamino-8-hydroxy-1,2,3,4-tetrahydro-naphthalene-2-carboxylate in 10 ml of THF/methanol/water (3:1:1) was treated with 695 mg of lithium hydroxide.1 H$_2$O while cooling with ice. The reaction mixture was stirred at 0° for 1 hour and at room temperature for 3 hours and then poured into a mixture of ice, 0.5N hydrochloric acid solution and chloroform. The aqueous phase was separated and exhaustively extracted with chloroform. The combined organic fractions were dried over sodium sulphate and concentrated. After drying the residue 555 mg (72%) of (S)-2-benzyloxycarbonyl-8-hydroxy-1,2,3,4-tetrahydro-naphthalene-2-carboxylic acid were obtained as a beige powder. M.p. 68°–75° (sintering). $[\alpha]_D=+83.5°$ (c=0.2, chloroform).

EXAMPLE 2.6.b 143 mg (0.576 mmol) of N-(benzyloxycarbonyl)-succinimide and 80.6 mg (0.96 mmol) of sodium hydrogen carbonate were added to a suspension of 100 mg (0.48 mmol) of (S)-2-amino-8-hydroxy-1,2,3,4-tetrahydro-naphthalene-2-carboxylic acid in 2 ml of dioxan/water (1:1). The reaction mixture was stirred at room temperature overnight, then again treated with 40 mg (0.336 mmol) of sodium hydrogen carbonate and 83.6 mg (0.48 mmol) of N-(benzyloxycarbonyl)-succinimide, stirred at room temperature for 4 hours and then poured into a mixture of saturated sodium chloride solution and ethyl acetate. The organic phase was separated, dried over $MgSO_4$ and concentrated. The residue was chromatographed on 20 g of silica gel with chloroform/methanol/water (6:3:0.5), whereupon after drying 66 mg (38.7%) of (S)-2-benzyloxycarbonyl-amino-8-hydroxy-1,2,3,4-tetrahydro-naphthalene-2-carboxylic acid were obtained as a beige powder. M.p. 65°–75° (sintering).

EXAMPLE 2.7.b

A solution of 620 mg (1.82 mmol) of (S)-benzyloxycarbonyl-amino-8-hydroxy-1,2,3,4-tetrahydro-naphthalene-2-carboxylic acid in 6 ml of N,N-dimethylformamide was treated at 0° with 521 mg (2.73 mmol) of N-ethyl-N'-(3-dimethylaminopropyl)-carbodiimide hydrochloride, 489 mg (3.64 mmol) of 1-N-hydroxylbenzotriazole, 502 µl (2.91 mmol) of ethyldiisopropylamine and 627 µl (4.37 mmol) of trimethylsilylethanol. The reaction mixture was stirred at 0° for 1 hour, then treated with 50 mg of N,N-dimethylaminopyridine and a further 627 µl (4.37 mmol) of trimethylsilylethanol, thereupon stirred at room temperature for 24 hours and subsequently poured into a mixture of water and dichloromethane. The aqueous phase was acidified with 0.1N hydrochloric acid and exhaustively extracted with dichloromethane. The combined organic phases were dried over $MgSO_4$ and concentrated. The residue was chromatographed on 100 g of silica gel with hexane/ethyl acetate (4:1→1:1), whereupon after drying 449 mg (56%) of trimethylsilylethyl (S)-2-benzyloxycarbonylamino-8-hydroxy-1,2,3,4-tetrahydro-naphthalene-2-carboxylate were obtained. M.p. 141°–144°. $[\alpha]_D$=+68.0° (c=0.2, chloroform).

EXAMPLE 2.8.b 1.2 ml (9.50 mmol) of trimethylchlorosilane were added under argon and while cooling with ice to a suspension of 513 mg (2.68 mmol) of (S)-2-amino-8-hydroxy-1,2,3,4-tetrahydro-naphthalene-2-carboxylic acid in 10 ml of dichlormethane. The reaction mixture was heated at reflux for 30 minutes, cooled, treated at 0° with 1.7 ml (9.92 mmol) of ethyldiisopropylamine, subsequently stirred at room temperature for 15 minutes and under reflux for 2 hours, then cooled to 0° and finally treated with a solution of 650 mg (2.98 mmol) of di-tert.butyl dicarbonate in 0.6 ml of dichloromethane. The reaction mixture was stirred at room temperature for 40 hours and under reflux for 7 hours, then cooled and subsequently poured into a mixture of 40 ml of saturated sodium hydrogen carbonate solution and diethyl ether. The organic phase was separated and extracted twice with 30 ml of saturated sodium hydrogen carbonate solution. The combined aqueous phases were adjusted to pH 4 while cooling with ice and extracted three times with 100 ml of ethyl acetate. The combined organic phases were dried over $Na_2SO_4$ and concentrated, whereupon after drying in a high vacuum 820 mg (99.6%) of (S)-2-(tert.butoxycarbonylamino)-8-hydroxy-1,2,3,4-tetrahydro-naphthalene-2-carboxylic acid were obtained as an amorphous solid. $[\alpha]_D$=+66.0° (c=1.0, chloroform). IR(KBr): 3403m(br.), 3033w, 2979w, 2933w, 1717s, 1695s, 1589w, 1500w, 1467m, 1395m, 1368m, 1278m, 1164m, 1063w, 776w.

EXAMPLE 2.9.a

A solution of 465 mg (1.45 mmol) of methyl (R)-2-(tert.butoxycarbonylamino)-8-hydroxy-1,2,3,4-tetrahydro-naphthalene-2-carboxylate in 4.5 ml of tetrahydrofuran/methanol/water (3:1:1) was treated with 647 mg of lithium hydroxide.1$H_2O$ while cooling with ice. The reaction mixture was stirred at 0° for 30 minutes and at room temperature for 2 hours and then poured into a mixture of chloroform/methanol (6:1) and 0.5N hydrochloric acid/ice. The organic phase was separated, dried over $MgSO_4$ and concentrated, whereupon after drying in a high vacuum 410 mg (92%) of (R)-2-(tert.butoxycarbonylamino)-8-hydroxy-1,2,3,4-tetrahydro-naphthalene-2-carboxylic acid were obtained as an amorphous solid. $[\alpha]_D$=−65.0° (c=0.5, chloroform).

EXAMPLE 2.10.b

A suspension of 770 mg (250 mmol) of (S)-2-(tert.butoxycarbonylamino)-8-hydroxy-1,2,3,4-tetrahydro-naphthalene-2-carboxylic acid in 5 ml of toluene was treated with 1.80 ml (7.52 mmol) of N,N-dimethylformamide di-tert.butyl acetal. The reaction mixture was stirred at 70° for 6 hours and then cooled, whereupon a further 0.6 ml (2.50 mmol) of N,N-dimethylformamide di-tert.butyl acetal was added and the mixture was stirred at 70° for 3 hours. The reaction mixture was poured into a mixture of ice-water and ethyl acetate, whereupon saturated sodium chloride solution was added. The aqueous phase was separated and extracted with ethyl acetate. The combined organic phases were dried over $Na_2SO_4$ and concentrated. The residue was chromatographed on 170 g of silica gel with ethyl acetate/hexane (1:4), whereupon after drying 665 mg (73%) of tert.butyl (S)-2-(tert.butoxycarbonylamino)-8-hydroxy-1,2,3,4-tetrahydro-naphthalene-2-carboxylate were obtained as an amorphous solid. $[\alpha]_D$=+65.5° (c=0.2, chloroform). IR(KBr): 3406m(br.), 2978m, 2932w, 1721s, 1695s, 1590m, 1497m, 1467m, 1394m, 1368s, 1303m, 1254m, 1162s, 1086m, 784w.

EXAMPLE 2.11.b

426 µl (2.86 mmol) of 1,8-diazabicyclo[5.4.2.0]undec-7-ene and 340 µl (2.86 mmol) of benzyl bromide were added while cooling with ice to a solution of 800 mg (2.60 mmol) of (S)-2-(tert.butoxycarbonylamino)-8-hydroxy-1,2,3,4-tetrahydro-naphthalene-2-carboxylic acid in 6 ml of N,N-dimethylformamide. The reaction mixture was stirred at room temperature for 18 hours and then poured on to ice-water, whereupon the mixture was exhaustively extracted with ethyl acetate. The combined organic phases were washed with saturated sodium chloride solution, dried over magnesium sulphate and concentrated. The residue was chromatographed on 120 g of silica gel with hexane/ethyl acetate (7:3), whereupon after drying in a high vacuum 829 mg (80.5%) of benzyl (S)-(tert.butoxycarbonylamino)-8-hydroxy-1,2,3,4-tetrahydro-naphthalene-2-carboxylate were obtained as a white foam. M.p. 51°–65° (sintering). $[\alpha]_D$=+64.5° (c=0.2, chloroform).

EXAMPLE 2.12.a

A solution of 440 mg (1.43 mmol) of (R)-2-(tert.butoxycarbonylamino)-8-hydroxy-1,2,3,4-tetrahydro-naphthalene-2-carboxylic acid in 8 ml of dichloromethane was treated with 140 µl of phenyldiazomethane. The reaction mixture was stirred at room temperature for 1 hour and then concentrated. The residue was chromatographed on 50 g of silica gel with chloroform, whereupon 384 mg (70%) of benzyl (R)-2-(tert.butoxycarbonylamino)-8-hydroxy-1,2,3,4-tetrahydro-naphthalene-2-carboxylate were obtained as an amorphous solid. M.p. 56°–60°. $[\alpha]_D$=−62.7° (c=1, chloroform).

EXAMPLE 3.1.b 110 mg (0.62 mmol) of N-bromosuccinimide were added portionwise under argon and while cooling with ice to a solution of 200 mg (0.62 mmol) of methyl (S)-2-(tert.butoxycarbonylamino)-8-hydroxy-1,2,3,4-tetrahydronaphthalene-2-carboxylate in 4 ml of trifluoroethanol. The reaction mixture was stirred at 0° for 1 hour and at room temperature for 1 hour and then poured into a mixture of saturated sodium hydrogen carbonate solution and chloroform. The organic phase was separated, washed with sodium chloride solution, dried over $MgSO_4$ and concentrated. The residue was chromatographed on 60 g of silica gel with ethyl acetate/hexane (1:9→4:6), whereupon after drying in a high vacuum 220 mg (88.6%) of methyl (S)-5-bromo-2-(tert.butoxycarbonylamino)-8-hydroxy-1,2,3,4-tetrahydronaphthalene-2-carboxylate were obtained. M.p. >180° (dec.). MS: 400 ($M^+$·, <1), 343(2), 284, 282(100), 144(52), 57(96).

EXAMPLE 4.1.1.a

A solution of 496 mg (1.30 mmol) of benzyl (R)-2-tert.butoxycarbonylamino-8-hydroxy-1,2,3,4-tetrahydronaphthalene-2-carboxylate in 1 ml of pyridine was treated while cooling with ice and under argon with 59.5 mg (1.37 mmol) of sodium hydride dispersion (55%). The mixture was stirred at 0° for 30 minutes, treated with 748 mg (3.64 mmol) of copper bromide-dimethyl sulphide complex and with 971 mg (3.90 mmol) of 2-iodonitrobenzene, brought to room temperature, stirred at 80° for 3 hours and at 120° for 4 hours, cooled and poured into a mixture of ice, 0.5N hydrochloric acid and ethyl acetate. The organic phase was separated, washed with 0.5N hydrochloric acid and saturated sodium chloride solution, dried over $MgSO_4$ and concentrated. The residue was chromatographed on silica gel (80 g) with ethyl acetate/hexane (5:95→1:1), whereupon after drying in a high vacuum 284 mg (44.8%) of benzyl (R)-2-tert.butoxycarbonylamino-8-(2-nitrophenoxy)-1,2,3,4-tetrahydronaphthalene-2-carboxylate were obtained as a beige amorphous solid. $[\alpha]_D=-52.3°$ (c=0.7, chloroform). MS: 427 (M-Bu; 5), 91(100), 57(46), 292(41), 283(25), 401(16).

EXAMPLE 4.1.2.a

A solution of 257 mg (0.49 mmol) of benzyl (R)-2-tert.butoxycarbonylamino-8-(2-nitrophenoxy)-1,2,3,4-tetrahydronaphthalene-2-carboxylate in 10 ml of methanol was added to a pre-hydrogenated suspension of 30 mg of Raney-nickel in 1 ml of methanol, whereupon the mixture was hydrogenated at room temperature for 45 minutes. The mixture was filtered over CELITE® and concentrated, whereupon after chromatography on 50 g of silica gel with ethyl acetate/hexane (1:9→1:4) and drying in a high vacuum 182 mg (75.2%) of benzyl (R)-8-(2-aminophenoxy)-2-tert.butoxycarbonylamino-1,2,3,4-tetrahydronaphthalene-2-carboxylate were obtained as a white solid. M.p. 58°–60°. $[\alpha]_D=-55.6°$ (c=0.2, chloroform).

EXAMPLE 4.1.3.a

A mixture of 169 mg (0.35 mmol) of (R)-8-(2-aminophenoxy)-2-tert.butoxycarbonylamino-1,2,3,4-tetrahydronaphthalene-2-carboxylate and 423.5 mg (1.04 mmol) of Fmoc-L-alanine N-hydroxysuccinimide ester in 2 ml of tetrahydrofuran was stirred at 50° for 3 days and then concentrated. The residue was chromatographed on 30 g of silica gel with hexane/ethyl acetate (95:5→4:1), whereupon after drying in a high vacuum 100 mg (37%) of benzyl (R)-2-tert.butoxycarbonylamino-8-[2-[(S)-2-9H-fluoren-9-ylmethoxycarbonylamino-propionylamino]-phenoxy]-1,2,3,4-naphthalene-2-carboxylate were obtained as a beige solid. M.p. 121°–124°. $[\alpha]_D=-44.0°$ (c=0.2, chloroform).

EXAMPLE 4.1.4.a 2 drops of diethylamine were added to a solution of 95 mg (0.121 mmol) of benzyl (R)-2-tert.butoxycarbonylamino-8-[2-[(S)-2-9H-fluoren-9-ylmethoxycarbonylamino-propionylamino]-phenoxy]-1,2,3,4-naphthalene-2-carboxylate in 2 ml of N,N-dimethylformamide, whereupon the mixture was stirred at room temperature for 15 hours. The reaction mixture was concentrated and the residue was chromatographed on 20 g of silica gel with dichloromethane, whereupon after drying 48 mg (71%) of benzyl (R)-8-[2-[(S)-2-amino-propionylamino]-phenoxy]-2-tert.butoxycarbonylamino-1,2,3,4-tetrahydronaphthalene-2-carboxylate were obtained as a white solid. M.p. 60°–62°. $[\alpha]_D=-3.5°$ (c=0.2, chloroform).

EXAMPLE 4.1.5.a

18 μl (0.1 1 mmol) of ethyldiisopropylamine were added at 0° to a solution of 41 mg (0.073 mmol) of benzyl (R)-8-[2-[(S)-2-amino-propionylamino]-phenoxy]-2-tert.butoxycarbonylamino-1,2,3,4-tetrahydro-naphthalene-2-carboxylate, 24.5 mg (0.11 mmol) of Z-L-alanine, 29 mg (0.22 mmol) of 1-hydroxybenzotriazole and 21 mg (0.11 mmol) of N-ethyl-N'-(3-dimethylaminopropyl)carbodiimide hydrochloride in 1 ml of N,N-dimethylformamide, whereupon the mixture was stirred at room temperature for 3 hours. The reaction mixture was poured into water and saturated sodium chloride solution, whereupon the pH was adjusted to 3 and the mixture was extracted with chloroform. The organic phase was concentrated and the residue was chromatographed on 10 g of silica gel with chloroform/methanol (98:2→chloroform), whereupon after drying 36.0 mg (64%) of benzyl (R)-8-[2-[(S)-2-[(S)-2-benzyloxycarbonylamino-propionylamino]-propionylamino]-phenoxy]-2-tert.butoxycarbonylamino-1,2,3,4-tetrahydro-naphthalene-2-carboxylate were obtained as a white solid. $[\alpha]_D=-62.0°$ (c=0.2, chloroform). MS: (ISP) 403.6 ($MH^+$).

EXAMPLE 4.1.6.a 10 mg of palladium-charcoal (10%) were added to a solution of 32.0 mg (0.042 mmol) of benzyl (R)-8-[2-[(S)-2-[(S)-2-Benzyloxycarbonylamino-propionylamino]-propionylamino]-phenoxy]-2-tert.butoxycarbonylamino-1,2,3,4-tetrahydro-naphthalene-2-carboxylate in 3 ml of 2,2,2-trifluoroethanol, whereupon the mixture was hydrogenated at room temperature for 2 hours. The suspension was filtered over cotton wool and concentrated. The residue was suspended several times with 2,2,2-trifluoroethanol, filtered off and dried in a high vacuum, 24 mg (>100%) (R)-8-[2-[(S)-2-[(S)-2-amino-propionylamino]-propionylamino]-phenoxy]- 2-tert.butoxycarbonylamino-1,2,3,4-tetrahydro-naphthalene-2-carboxylic acid being obtained as a beige solid. M.p. 210°–212°. MS: (LDP) 541.8 ($MH^+$; 9) 563.7 ($M+Na^+$; 100).

EXAMPLE 4.1.7.a 18.6 mg (0.22 mmol) of dried $NaHCO_3$ were added at 0° to a solution of 24.0 mg (0.044 mmol) of (R)-8-[2-[(S)-2-[(S)-2-amino-propionylamino]-propionylamino]-phenoxy]-

2-tert.butoxycarbonylamino-1,2,3,4-tetrahydro-naphthalene-2-carboxylic acid and 42.5 mg (0.132 mmol) of 1,1,3,3-tetramethyl-2-[1H-1,2,3-triazolo[5,4-b]pyridin-1-yl] uronium tetrafluoroborate (TATU) in 133 ml of N,N-dimethylformamide, whereupon the mixture was stirred at 0° for 4 hours. The solvent was distilled off in a high vacuum and the residue was taken up in chloroform and water, whereupon the organic phase was washed with water, dried with MgSO$_4$ and concentrated. The residue was chromatographed on 10 g of silica gel with chloroform→chloroform/methanol (95:5), whereupon after drying 14.2 mg (61.7%) of tert.butyl (12S,15S,18R)-(12,15-dimethyl-11,14,17-trioxo-10,11,12,13,14,15,16,17,18,19,20,21-dodecahydro-1,18-etheno-dibenz[b,n][1,5,8,11]oxatriazacyclopentadecin-18-yl)-carbamate were obtained as a white solid. MS: (LDP) 522.6 (4), 545.5 (M+Na$^+$; 100).

EXAMPLE 4.1.8.a 0.2 ml of trifluoroacetic acid was added dropwise at 0° to a solution of 12.5 mg (0.024 mmol) of tert.butyl (12S,15S,18R)-(12,15-dimethyl-11,14,17-trioxo-10,11,12,13,14,15,16,17,18,19,20,21-dodecahydro-1,18-etheno-dibenz[b,n][1,5,8,11 ]oxatriazacyclopentadecin-18-yl)-carbamate in 0.2 ml of dichloromethane, whereupon the mixture was stirred at 0° for 2 hours. The reaction mixture was concentrated to dryness. The residue was dried in a high vacuum, re-precipitated from dichloromethane, filtered off and dried in a high vacuum, whereupon 13.1 mg (100%) of (12S,15S,18R)-18-amino-12,15-dimethyl-10,11,12,13,14,15,16,17,18,19,20,21-dodecahydro-1,18-etheno-dibenz[b,n][1,5,8,11]oxatriazacyclopentadecine-11,14,17-trione trifluoroacetate (1:1). MS: (LDP) 445.2 (M+Na$^+$; 100).

EXAMPLE 4.2.1.a 52 mg (1.2 mmol) of sodium hydride dispersion (55%) were added at 0° and under argon to a solution of 374 mg (0.98 mmol) of benzyl (R)-2-tert.butoxycarbonylamino-8-hydroxy-1,2,3,4-tetrahydronaphthalene-2-carboxylate in 3 ml of dioxan, whereupon the mixture was stirred for 30 minutes. Thereafter, 63 mg (20 mol %) of tris-[2-(2-methoxyethoxy)-ethyl]amine (TDA I) and 311 mg (1.96 mmol) of 2-chloro-3-nitropyridine were added, whereupon the mixture was stirred at 120° for 1 hour. The reaction mixture was poured into saturated ammonium chloride solution and ethyl acetate. The organic phase was washed with saturated NaCl solution, dried with Na$_2$SO$_4$ and concentrated. The residue was chromatographed or 50 g of silica gel with chloroform, whereupon after drying 328 mg (65%) of benzyl (R)-2-tert.butoxycarbonylamino-8-(3-nitro-2-pyridoxy)-1,2,3,4-tetrahydronaphthalene-2-carboxylate were obtained as a beige solid. M.p. 64°–66°. MS: 463 (M-=<, 1), 402 (24), 293 (21), 284 (36), 250 (21), 145 (17), 91 (100), 57 (85).

EXAMPLE 4.2.2.a

A solution of 300 mg (0.577 mmol) of benzyl (R)-2-tert.butoxycarbonylamino-8-(3-nitro-2-pyridoxy)-1,2,3,4-tetrahydronaphthalene-2-carboxylate in 10 ml of methanol was added to a pre-hydrogenated suspension of 100 mg of Raney-nickel in 2 ml of methanol, whereupon the mixture was hydrogenated for 1 hour. The mixture was filtered over CELITE® and concentrated, and the residue was dissolved in 5 ml of dichloromethane, whereupon phenyldiazomethane was added until the red colour remained constant. The solvent was evaporated and the residue was chromatographed on 50 g of silica gel with ethyl acetate/hexane (1:3), whereupon after drying in a high vacuum 256 mg (90.5%) of benzyl (R)-8-(3-amino-2-pyridoxy)-2-tert.butoxycarbonylamino-1,2,3,4-tetrahydronaphthalene-2-carboxylate were obtained as a white amorphous solid. M.p. 71°–73°. [α]$_D$=–37.9° (c=1, chloroform).

EXAMPLE 4.2.3.a 600 mg (1.47 mmol) of Fmoc-L-alanine N-hydroxysuccinimide ester were added to a solution of 239 mg (0.49 mmol) of benzyl (R)-8-(3-amino-2-pyridoxy)-2-tert.butoxycarbonylamino-1,2,3,4-tetrahydronaphthalene-2-carboxylate in 1 ml of tetrahydrofuran, whereupon the mixture was stirred at 50° for 32 hours. The mixture was concentrated, the residue was taken up in water and ethyl acetate, the organic phase was separated, washed with H$_2$O, dried with Na$_2$SO$_4$ and concentrated, and the residue was chromatographed on 50 g of silica gel with hexane/isopropanol (9:1), whereupon after drying in a high vacuum 268 mg (70%) of benzyl (R)-2-tert.butoxycarbonylamino-8-[3-[(S)-2-9H-fluoren-9-ylmethoxycarbonylamino]-pyridin-2-yloxy]-1,2,3,4-tetrahydronaphthalene-2-carboxylate were obtained as a beige solid. M.p. 125°–130°. [α]$_D$=–34.8° (c=1, chloroform).

EXAMPLE 4.2.4.a

In analogy to Example 4.1.4.a, 247 mg (0.315 mmol) of benzyl (R)-2-tert.butoxycarbonylamino-8-[3-[(S)-2-9H-fluoren-9-ylmethoxycarbonylamino]-pyridin-2-yloxy]-1,2,3,4-tetrahydronaphthalene-2-carboxylate in 4 ml of N,N-dimethylformamide were reacted with 0.6 ml of diethylamine and the residue was chromatographed on 40 g of silica gel with dichloromethane, whereupon after drying in a high vacuum 179 mg of benzyl (R)-8-[3-[(S)-2-aminopropionylamino]pyridin-2-yloxy]-2-tert.butoxycarbonylamino-1,2,3,4-tetrahydronaphthalene-2-carboxylate were obtained.

To 169 mg (0.30 mmol) of this product dissolved in 2 ml of tetrahydrofuran were added 144 mg (0.45 mmol) of Z-L-alanine N-hydroxysuccinimide ester, whereupon the mixture was stirred at room temperature for 3 hours. The reaction mixture was concentrated and the residue was chromatographed on 50 g of silica gel with hexane/ethyl acetate (1:4→1:1), whereupon after drying in a high vacuum 181 mg (78.4%) of benzyl (R)-8-[3-[(S)-2-[(S)-2-benzyloxycarbonylamino-propionylamino]-propionylamino]-pyridin-2-yloxy]-2-tert.butoxycarbonylamino-1,2,3,4-tetrahydro-naphthalene-2-carboxylate were obtained as a white powder. M.p. 172°–176°. [α]$_D$=–59.8° (c=1, chloroform).

EXAMPLE 4.2.5.a 30 mg of palladium-charcoal (10%) were added to a solution of 168 mg (0.22 mmol) of benzyl (R)-8-[3-[(S)-2-[(S)-2-benzyloxycarbonylamino-propionylamino]-propionylamino]-pyridin-2-yloxy]-2-tert.butoxycarbonylamino-1,2,3,4-tetrahydro-naphthalene-2-carboxylate in 10 ml of methanol, whereupon the mixture was hydrogenated at room temperature for 2 hours. The reaction mixture was filtered over CELITE®, the filtrate was concentrated and the solid residue was suspended in diethyl ether while stirring well, filtered off and dried in a high vacuum, whereupon 120 mg (~100%) of (R)-8-[3-[(S)-2-[(S)-2-amino-propionylamino]-propionylamino]-pyridin-2-yloxy]-2-tert.butoxycarbonylamino-1,2,3,4-tetrahydro-naphthalene-2-carboxylic acid were obtained as a white powder. M.p. 239°–241°. MS: (ISN) 540.2, 100% (MH$^-$), 596.0, (53), (MH$^-$) (Ni).

EXAMPLE 4.2.6.a 170 mg (0.447 mmol) of O-benzotriazol-1-yl-N,N,N',N'-tetramethyl-uronium hexafluorophosphate (HBTU) and 62 mg (0.745 mmol) of dried NaHCO$_3$ were added at 0° to a solution of 81 mg (0.149 mmol) of (R)-8-[3-[(S)-2-[(S)-2-amino-propionylamino]-propionylamino]-pyridin-2-yloxy]-2-tert.butoxycarbonylamino-1,2,3,4-tetrahydronaphthalene-2-carboxylic acid in 250 ml of N,N-dimethylformamide, whereupon the mixture was stirred at 0° for 3 hours. The reaction mixture was concentrated, the residue was taken up in water and ethyl acetate, the organic phase was washed three times with saturated NaHCO$_3$ solution, dried over Na$_2$SO$_4$ and concentrated, and the residue was chromatographed on 30 g of silica gel with chloroform/methanol (98:2), whereupon after drying in a high vacuum 50 mg (64%) of tert.butyl (12S,15S,18R)-(12,15-dimethyl-11,14,17-trioxo-10,11,12,13,14,15,16,17,18,19,20,21-dodecahydro-1,18-etheno-pyrido[2,3-b]benz[n][1,4,7,10]oxatriazacyclopentadecin-18-yl)-carbamate were obtained as a white powder. M.p. (dec.)=265°. [α]$_D$=−127.2° (c=0.5, chloroform).

EXAMPLE 4.2.7.a 3 ml of trifluoroacetic acid were added dropwise at 0° to a solution of 50.6 mg (0.095 mmol) of (12S,15S,18R)-(12,15-dimethyl-11,14,17-trioxo-10,11,12,13,14,15,16,17,18,19,20,21-dodecahydro-1,18-etheno-pyrido[2,3-b]benz[n][1,4,7,10]oxatriazacyclopentadecin-18-yl)-carbamate in 3 ml of dichloromethane, whereupon the mixture was stirred at 0° for 3 hours. The mixture was concentrated in a high vacuum and the residue was suspended in diethyl ether/hexane (1:1), filtered off and dried in a high vacuum, whereupon 42.0 mg (81.8%) of (12S,15S,18R)-18-amino-12,15-dimethyl-10,11,12,13,14,15,16,17,18,19,20,21-dodecahydro-1,18-ethenopyrido[2,3-b]benz[n][1,4,7,10]oxatriazacyclopentadecine-11,14,17-trione trifluoroacetate (1:1) were obtained as a white powder. M.p. (dec.)= 212°–217°. [α]$_D$=−50.2° (c=1.0, chloroform).

EXAMPLE 4.3.1.a 74 mg (1.68 mmol) of sodium hydride dispersion (55%) were added at 0° under argon to a solution of 514 mg (1.6 mmol) of methyl (R)-2-tert.butoxycarbonylamino)-8-hydroxy-1,2,3,4-tetrahydronaphthalene-2-carboxylate in 2 ml of anhydrous dioxan, whereupon the mixture was stirred at 0° for 20 minutes. Subsequently, 100 mg (20 mol %) of tris-[2-(2-methoxyethoxy)-ethyl]amine (TDA I) and 1.28 g (4.8 mmol) of (S)-1-bromo-3-tert.butyldimethylsiloxy-2-methylpropane were added to the reaction mixture, whereupon it was stirred at 120° C. in a bomb tube for 30 minutes. Thereafter, the reaction mixture was cooled, treated with 14.8 mg of sodium hydride dispersion and stirred at 120° for a further 30 minutes. After cooling the reaction mixture was poured into ice-water and ethyl acetate; the organic phase was washed with water and saturated NaCl solution, dried over Na$_2$SO$_4$ and concentrated, and the residue was chromatographed on 120 g of silica gel with hexane/ethyl acetate (9:1→4:1), whereupon after drying in a high vacuum 312 mg (38.4%) of methyl (R)-2-tert.butoxycarbonylamino-8-[(S)-(3-tert.butyldimethylsiloxy-2-methyl-1-propyloxy)]-1,2,3,4-tetrahydronaphthalene-2-carboxylate were obtained as a colourless oil. [α]$_D$=−70.6° (c=1.0, chloroform). MS (ISP): 525.6 (M+NH$_4^+$; 100), 508.6 (M+H$^+$; 50).

EXAMPLE 4.3.2.a 560 mg (1.77 mmol) of tetrabutylammonium fluoride were added at 0° to a solution of 300 mg (0.59 mmol) of methyl (R)-2-tert.butyloxycarbonylamino-8-[(S)-(3-tert.butyldimethylsilyoxy-2-methyl-1-propyloxy)]-1,2,3,4-tetrahydronaphthalene-2-carboxylate in 2 ml of tetrahydrofuran, whereupon the mixture was stirred for 3 hours. The reaction mixture was poured into ice-water and ethyl acetate, the organic phase was washed with water, dried with Na$_2$SO$_4$ and concentrated, and the residue was chromatographed on 40 g of silica gel with ethyl acetate/hexane (1:4→1:1), whereupon after drying in a high vacuum 183 mg (78.7%) of methyl (R)-2-tert.butoxycarbonylamino-8-[(S)-(3-hydroxy-2-methylpropyloxy)]-1,2,3,4-tetrahydronaphthalene-2-carboxylate was obtained as a colourless oil. MS (ISP): 411.5 (M+NH$_4^+$; 100), 394.4 (M+H$^+$; 62), 338.4 (13).

EXAMPLE 4.3.3.a 95.3 mg (0.5 mmol) of tosyl chloride and a spatula tip of 4-(N,N-dimethylamino)-pyridine were added at 0° under argon to a solution of 179 mg (0.455 mmol) of methyl (R)-2-tert.butoxycarbonylamino-8-[(S)-3-hydroxy-2-methylpropyloxy)]-1,2,3,4-tetrahydronaphthalene-2-carboxylate and 92 mg (0.91 mmol) of triethylamine in 3 ml of dichloromethane. The reaction mixture was stirred at 0° for 2 hours and at room temperature for 15 minutes, whereupon 46 mg (0.45 mmol) of triethylamine and 48 mg (0.25 mmol) of tosyl chloride were again added and the mixture was stirred at room temperature for 2 hours. The reaction mixture was poured into ice-water and ethyl acetate, the organic phase was washed with water, dried over Na$_2$SO$_4$ and concentrated, and the residue was chromatographed on SiO$_2$ with ethyl acetate/hexane (1:4→1:1), whereupon after drying in a high vacuum 127 mg (51%) of methyl (R)-2-tert.butoxycarbonylamino-8-[(R)-2-methyl-2-(4-methyl-phenylsulphonyloxy)-propoxy]-1,2,3,4-tetrahydronaphthalene-2-carboxylate were obtained as a white solid. M.p. 55°–58°. MS (ISP): 565.1 (M+NH$_4^+$; 90), 548.1 (M+H$^+$; 100), 448.0 (95).

EXAMPLE 4.3.4.a 25 mg (0.48 mmol) of ammonium chloride were added to a solution of 120 mg (0.182 mmol) of methyl (R)-2-tert.butoxycarbonylamino-8-[(R)-2-methyl-2-(4-methyl-phenylsulphonyloxy)-propoxy]-1,2,3,4-tetrahydronaphthalene-2-carboxylate and 142 mg (2.13 mmol) of sodium azide in 1.5 ml of methanol, whereupon the mixture was stirred at 70° for 3 hours. Thereafter, 142 mg (2.19 mmol) of sodium azide and 25 mg of ammonium chloride were again added and the mixture was stirred at 70° for a total of 12 hours. The reaction mixture was concentrated, the residue was taken up in water and ethyl acetate, the organic phase was washed with water, dried with Na$_2$SO$_4$ and concentrated, and the residue was chromatographed on silica gel with ethyl acetate/hexane (1:9), whereupon after drying in a high vacuum 89 mg (97%) of methyl (R)-8-[(S)-3-azido-2-methyl-propoxy]-2-tert.butoxycarbonylamino-1,2,3,4-tetrahydronaphthalenecarboxylate were obtained as a colourless resin. MS (ISP): 419.4 (M+H$^+$; 50), 319.2 (100).

EXAMPLE 4.3.5.a 50 mg of palladium-charcoal (10%) were added to a solution of 83 mg (0.198 mmol) of methyl (R)-8-[(S)-3-azido-2-methyl-propoxy]-2-tert.butoxycarbonylamino-1,2,3,4-tetrahydronaphthalenecarboxylate in 5 ml of ethanol, whereupon the mixture was hydrogenated at room temperature for 2 hours. The reaction mixture was filtered over CELITE® and was subsequently again hydrogenated twice in the same manner. The solution was concentrated and dried in a high vacuum, with 71 mg of a mixture of methyl (R)-8-[(S)-3-amino-2-methyl-propoxy]-2-tert.butoxycarbonylamino-1,2,3,4-tetrahydronaphthalene-2-carboxylate and methyl (R)-2-tert.butoxycarbonylamino-8-[(S)-3-ethylamino-2-methyl-propoxy]-1,2,3,4-tetrahydronaphthalene-2-carboxylate being obtained. MS (ISP): 421.5 (M+H$^+$; 92), 393.5 (M+H$^+$; 100).

EXAMPLE 4.3.6.a

In analogy to Example 4.1.5.a, 70 mg (~0.178 mmol) of a mixture of methyl (R)-8-[(S)-3-amino-2-methyl-propoxy]-2-tert.butoxycarbonylamino-1,2,3,4-tetrahydronaphthalene-2-carboxylate and methyl (R)-2-tert.butoxycarbonylamino-8-[(S)-3-ethylamino-2-methyl-propoxy]-1,2,3,4-tetrahydronaphthalene-2-carboxylate in 1.5 ml of N,N-dimethylformamide were reacted at 0° for 3 hours with 78 mg (0.267 mmol) of Z-L-alanylalanine, 114 mg (0.356 mmol) of O-(1,2-dihydro-2-oxo-1-pyridyl)-N,N,N',N'-tetramethyl-uronium tetrafluoroborate (TPTU), 54.5 mg (0.356 mmol) of 1-hydroxybenzotriazole and 86 µl (0.534 mmol) of ethyldiisopropylamine. The residue was chromatographed on 20 g of silica gel with chloroform→chloroform/methanol (95:5→4:1), whereupon after drying in a high vacuum 30 mg (40.3%) of methyl (R)-8-[(S)-3-[[(S)-2-[(S)-2-benzyloxycarbonylamino-propionylamino]-propionyl]-ethyl-amino]-2-methyl-propoxy]-2-tert.butoxycarbonylamino-1,2,3,4tetrahydronaphthalene-2-carboxylate, [MS (ISP): 697.6 (M+H$^+$; 100)], and then 26 mg (21.8%) of methyl (R)-8-[(S)-3-[(S)-2-[(S)-2-benzyloxycarbonylamino-propionylamino]-propionylamino]-2-methyl-propoxy]-2-tert.butoxycarbonylamino-1,2,3,4-tetrahydronaphthalene-2-carboxylate [MS (ISP): 535.5 (M+H$^+$; 100)] were obtained.

EXAMPLE 4.3.7.a 15 mg of palladium-charcoal (10%) were added to a solution of 28.0 g (42. µmol) of methyl (R)-8-[(S)-3-[(S)-2-[(S)-2-benzyloxycarbonylamino-propionylamino]-propionylamino]-2-methyl-propoxy]-2-tert.butoxycarbonylamino-1,2,3,4-tetrahydronaphthalene-2-carboxylate in 5 ml of 2,2,2-trifluoroethanol and 2 drops of water, whereupon the mixture was hydrogenated at room temperature for 1 hour. The reaction mixture was filtered over CELITE®, the filtrate was concentrated and the residue was dried in a high vacuum, whereupon 19 mg (84.8%) of methyl (R)-8-[(S)-3-[(S)-2-[(S)-amino-propionylamino]-propionylamino]-2-methyl-propoxy]-2-tert.butoxycarbonylamino-1,2,3,4-tetrahydronaphthalene-2-carboxylate were obtained as a colourless lacquer. MS (ISP): 535.5 (M+H$^+$; 100).

EXAMPLE 4.3.8.a

123 µl of a 1N aqueous lithium hydroxide solution were added to a solution of 19.0 mg (35.0 mmol) of methyl (R)-8-[(S)-3-[(S)-2-[(S)-amino-propionylamino]-propionylamino]-2-methyl-propoxy]-2-tert.butoxycarbonylamino-1,2,3,4-tetrahydronaphthalene-2-carboxylate in 1 ml of tetrahydrofuran/methanol/water (3:1:1), whereupon the mixture was stirred at room temperature for 15 hours. Thereafter, a further 200 µl of 1N lithium hydroxide solution were added and the mixture was stirred at room temperature for 48 hours. The reaction mixture was made neutral using 2N HCl and was concentrated to dryness. The residue was chromatographed over a MCl gel column with water→water/methanol (95:5→4:1), whereupon after drying in a high vacuum 17 mg (91.9%) of (R)-8-[(S)-3-[(S)-2-[(S)-2-amino-propionylamino]-propionylamino]-2-methyl-propoxy]-2-tert.butoxycarbonylamino-1,2,3,4-tetrahydronaphthalene-2-carboxylic acid were obtained as a white powder. MS (ISP): 521.4 (M+H$^+$; 100).

EXAMPLE 4.3.9.a 9.6 mg (0.115 mmol) of NaHCO$_3$ were added to a solution of 12.0 mg (23.0 mmol) of (R)-8-[(S)-3-[(S)-2-[(S)-2-amino-propionylamino]-propionylamino]-2-methyl-propoxy]-2-tert.butoxycarbonylamino-1,2,3,4-tetrahydronaphthalene-2-carboxylic acid and 22.0 mg (70.0 mmol) of 1,1,3,3-tetramethyl-2-[1H-1,2,3-triazolo[5,4-b]pyridin-1-yl]uronium tetrafluoroborate (TATU) in 70 ml of anhydrous N,N-dimethylformamide, whereupon the mixture was stirred at room temperature for 15 hours and then concentrated. The residue was taken up in chloroform, the solution was washed with water, the organic phase was dried with Na$_2$SO$_4$ and concentrated, and the residue was chromatographed on 10 g of silica gel with chloroform→chloroform/methanol (98:2) whereupon after drying in a high vacuum 5.9 mg (50.9%) of tert.butyl (3S,7S,10S,13R)-(3,7,10-trimethyl-6,9,12-trioxo-3,4,5,6,7,8,9,10,11,12,13,14,19,20-tetradecahydro-13,15-etheno-2H-1,5,8,11-benzoxatriazacyclohexadecin-13-yl)-carbamate were obtained as a white powder. MS: 503.2 (M+H$^+$; 55), 91.1 (100), 216.9 (89), 109.1 (33), 149.0 (25).

EXAMPLE 4.3.10.a

In analogy to Example 4.1.8.a, 5.9 mg (12.0 mmol) of tert.butyl (3S,7S,10S,13R)-(3,7,10-trimethyl-6,9,12-trioxo-3,4,5,6,7,8,9,10,11,12,13,14,19,20-tetradecahydro-13,15-etheno-2H-1,5,8,11-benzoxatriazacyclohexadecin-13-yl)-carbamate in 0.5 ml of dichlormethane and 0.5 ml of trifluoroacetic acid were reacted at 0°, whereupon the residue, after precipitation from ether/hexane (1;1), was dried in a high vacuum. 6.0 mg (99.0%) of (3S,7S,10S,13R)-13-amino-3,7,10-trimethyl-3,4,5,6,7,8,9,10,11,12,13,14,19,20-tetradecahydro-13,15-etheno-2H-1,5,8,11-benzoxatriazacyclohexadecine-6,9,12-trione trifluoroacetate (1:1) were obtained as a white powder. MS (ISP): 403.5 (M+H$^+$; 100).

EXAMPLE 4.4.1.a

In analogy to Example 4.3.7.a, 25.0 mg (35.0 mmol) of methyl (R)-8-[(S)-3-[[(S)-2-[(S)-2-benzyloxycarbonylamino-propionylamino]-propionyl]-ethyl-amino]-2-methyl-propoxy]-2-tert.butoxycarbonylamino-1,2,3,4-tetrahydronaphthalene-2-carboxylate in 3 ml of 2,2,2-trifluoroethanol and 15 mg of palladium-charcoal (10%) were hydrogenated at room temperature for 2 hours. After working up according to Example 4.3.7.a and drying in a high vacuum 18.0 mg (90%) of methyl (R)-8-[(S)-3-[[(S)-2-[(S)-2-amino-propionylamino]-propionyl]-ethyl-amino]-2-methyl-propoxy]-2-tert.butoxycarbonylamino-1,2,3,4-tetrahydronaphthalene-2-carboxylate were obtained as a colourless oil. MS (ISP): 563.4 (M+H$^+$; 100).

EXAMPLE 4.4.2.a

In analogy to Example 4.3.8.a, 18.0 mg (32.0 mmol) of methyl (R)-8-[(S)-3-[[(S)-2-[(S)-2-amino-propionylamino]-propionyl]-ethyl-amino]-2-methyl-propoxy]-2- tert.butoxycarbonylamino-1,2,3,4-tetrahydronaphthalene-2-carboxylate in 1 ml of tetrahydrofuran/methanol/water (3:1:1) were reacted with 320 µl of 1N lithium hydroxide solution. After working up and purification according to Example 4.3.8.a 17.0 mg (96.8%) of (R)-8-[(S)-3-[(S)-2-[(S)-2-amino-propionylamino]-propionyl]-ethyl-amino]-2-methyl-propoxy]-2-tert.butoxycarbonylamino-1,2,3,4-tetrahydronaphthalene-2-carboxylic acid were obtained as a white powder. MS: 549 (M+H$^+$), 216.9 (100), 91.1 (75), 149.0 (36), 513 (35), 471 (31), 109 (29).

EXAMPLE 4.4.3.a

In analogy to Example 4.1.7.a, 18.0 mg (32.0 µmol) of (R)-8-[(S)-3-[[(S)-2-[(S)-2-amino-propionylamino]-propionyl]-ethyl-amino]-2-methyl-propoxy]-2-tert.butoxycarbonylamino-1,2,3,4-tetrahydronaphthalene-2-carboxylic acid were reacted at 0° for 15 hours with 31.0 mg (99.0 µmol) of 1,1,3,3-tetramethyl-2-[1H-1,2,3-triazolo[5,4-b]pyridin-1-yl]-uronium tetrafluoroborate (TATU) and 13.8 mg (0.165 mmol) of NaHCO$_3$ in 100 ml of anhydrous N,N-dimethylformamide. After working up according to Example 4.1.7.a, chromatography on 5 g of silica gel with chloroform→chloroform/methanol (98:2) and drying in a high vacuum 12.9 mg (74.1%) of tert.butyl (3S,7S,10S,13R)-(5-ethyl-3,7,10-trimethyl-6,9,12-trioxo-13,15-etheno-3,4,5,6,7,8,9,10,11,12,13,14,19,10-tetradecahydro-2H-1,5,8,11-benzoxatriazacyclohexadecin-13-yl)-carbamate were obtained as a white powder. MS (ISP): 531.6 (M+H$^+$; 100), 553.6 (M+Na$^+$; 52).

EXAMPLE 4.4.4.a

In analogy to Example 4.1.8.a, 12.9 mg (24.0 µmol) of tert.butyl (3S,7S,10S,13R)-(5-ethyl-3,7,10-trimethyl-6,9,12-trioxo-13,15-etheno-3,4,5,6,7,8,9,10,11,12,13,14,19,10-tetradecahydro-2H-1,5,8,11-benzoxatriazacyclohexadecin-13-yl)-carbamate in 0.2 ml of dichloromethane and 0.2 ml of trifluoroacetic acid were reacted at 0°, whereupon the mixture was worked up and purified according to Example 4.1.8.a. The residue was suspended in ether/hexane (1:1), filtered off and dried in a high vacuum, whereupon 10.0 mg (75.8%) of: (3S,7S,10S,13R)-13-amino-5-ethyl-3,7,10-trimethyl-3,4,5,6,7,8,9,10,11,12,13,14,19,20-tetradecahydro-2H-1,5,8,11-benzoxatriazacyclohexadecine-6,9,12-trione trifluoroacetate (1:1) were obtained as a white powder. MS (LDP): 453.5 (M+Na$^+$; 100), 469.4 (M+K$^+$, 26), 431.5 (M+H$^+$; 4).

EXAMPLE 4.5.1.a 74 mg (1.68 mmol) of sodium hydride dispersion (55%) were added at 0° under argon to a solution of 514 mg (1.60 mmol) of methyl (R)-2-tert.butoxycarbonylamino-8-hydroxy-1,2,3,4-tetrahydronaphthalene-2-carboxylate in 2 ml of pyridine, whereupon the mixture was stirred for 20 minutes. Thereafter, 460 mg (2.24 mmol) of copper bromide-dimethyl sulphide complex and 1.54 g (4.8 mmol) of benzyl N-2-bromobenzyl-carbamate were added at 0°, whereupon the mixture was heated to 120° for 4 hours. The reaction mixture was cooled and poured into ice, 0.5N HCl and ethyl acetate, the organic phase was washed with water, dried with Na$_2$SO$_4$ and concentrated, and the residue was chromatographed on 100 g of silica gel with hexane/ethyl acetate (4:1→1:1), whereupon after drying in a high vacuum 368 mg (41%) of methyl (R)-8-(2-benzyloxycarbonyl-aminomethyl-phenoxy)-2-tert.butyloxycarbonylamino-1,2,3,4-tetrahydronaphthalene-2-carboxylate were obtained as a light yellow powder. M.p. 82°–85°. [α]$_D$=–92.0° (c=1, chloroform).

EXAMPLE 4.5.2.a

A solution of 324 mg (0.58 mmol) of methyl (R)-8-(2-benzyloxycarbonylaminomethyl-phenoxy)-2-tert.butoxycarbonyl-amino-1,2,3,4-tetrahydronaphthalene-2-carboxylate in 4 ml of ethanol was treated with 100 mg of palladium-charcoal (10%), whereupon the mixture was hydrogenated at room temperature for 3 hours. The reaction mixture was filtered over CELITE® and concentrated, and the residue was chromatographed on 30 g of silica gel with chloroform→chloroform/methanol (95:5), whereupon after drying in a high vacuum 211 mg (85.4%) of methyl (R)-8-(2-aminomethyl-phenoxy)-2-tert.butoxycarbonylamino-1,2,3,4-tetrahydronaphthalene-2-carboxylate were obtained as a white amorphous solid. M.p. 57°–59°. MS (ISP): 427.6 (M+H$^+$; 100).

EXAMPLE 4.5.3.a

In analogy to Example 4.1.5.a, 205 mg (0.48 mmol) of methyl (R)-8-(2-aminomethyl-phenoxy)-2-tert.butoxycarbonylamino-1,2,3,4-tetrahydronaphthalene-2-carboxylate in 5 ml of N,N-dimethylformamide were reacted at 0° for 5 hours with 212 mg (0.72 mmol) of Z-L-alanyl-L-alanine, 97 mg (0.72 mmol) of 1-hydroxybenzotriazole, 160 mg (0.84 mmol) of N-ethyl-N'-(3-dimethylaminopropyl)-carbodiimide hydrochloride and 216 µl (1.26 mmol) of ethyldiisopropylamine. The reaction mixture was concentrated in a high vacuum, the residue was taken up in water and ethyl acetate, the organic phase was washed with water, dried with Na$_2$SO$_4$ and concentrated, and the residue was chromatographed on 70 g of silica gel with chloroform/methanol (99:1), whereupon 193 mg (57.2%) of methyl (R)-8-[2-[(S)-2-[(S)-benzyloxycarbonylamino-propionylamino]-propionylaminomethyl]-phenoxy]-2-tert.butoxycarbonylamino-1,2,3,4-tetrahydronaphthalene-2-carboxylate were obtained as a white amorphous solid. M.p. 82°–84°. [α]$_D$=–80.0° (c=1, chloroform).

EXAMPLE 4.5.4.a 50 mg of palladium-charcoal (10%) were added to a solution of 250 mg (0.356 mmol) of methyl (R)-8-[2-[(S)-2-[(S)-benzyloxycarbonylamino-propionylamino]-propionylaminomethyl]phenoxy]-2-tert.butoxycarbonylamino-1,2,3,4-tetrahydronaphthalene-2-carboxylate in 5 ml of ethanol, whereupon the mixture was hydrogenated at room temperature for 1 hour. The mixture was filtered over CELITE® and concentrated, and the residue was chromatographed on 30 g of silica gel with chloroform/methanol (95:5), whereupon after drying in a high vacuum 169 mg (83.6%) of methyl (R)-8-[2-[(S)-[(S)-2-amino-propionylamino]propionylaminomethyl]-phenoxy]-2-tert.butoxycarbonylamino-1,2,3,4-tetrahydronaphthalene-2-carboxylate were obtained as a white solid. M.p. 125°–130°. [α]$_D$=–97.0° (c=1.0, chloroform).

EXAMPLE 4.5.5.a 47 mg (1.12 mmol) of lithium hydroxide monohydrate were added while cooling with ice to a solution of 128 mg (0.225 mmol) of methyl (R)-8-[2-[(S)-[(S)-2-amino-propionylamino]propionylaminomethyl]-phenoxy]-2-tert.butoxycarbonylamino-1,2,3,4-tetrahydronaphthalene-2-carboxylate in 1.5 ml of tetrahydrofuran/methanol/water (3:1:1), whereupon the mixture was stirred at room temperature for 24 hours. The reaction mixture was concentrated, the residue was dissolved in water and the solution was made neutral with 2N HCl and concentrated. The residue was chromatographed on MCl gel firstly with water and then with methanol/water (1:4), whereupon after drying in a high vacuum 106 mg (85%) of (R)-8-[2-[(S)-2-[(S)-2-amino-propionylamino]-propionylaminomethyl]-phenoxy]-2-tert.butoxycarbonylamino-1,2,3,4-tetrahydronaphthalene-2-carboxylic acid were obtained as a white powder. M.p. 222°–226°. $[\alpha]_D = -43.5°$ (c=0.2, methanol).

EXAMPLE 4.5.6.a 75.6 mg (0.90 mmol) of dried $NaHCO_3$ were added at 0° under argon to a solution of 100 mg (0.18 mmol) of (R)-8-[2-[(S)-2-[(S)-2-amino-propionylamino]-propionylaminomethyl]-phenoxy]-2-tert.butoxycarbonylamino-1,2,3,4-tetrahydronaphthalene-2-carboxylic acid and 204 mg (0.54 mmol) of O-benzotriazol-1-yl-N,N,N',N'-tetramethyl-uronium hexafluorophosphate (HBTU) in 220 ml of N,N-dimethylformamide, whereupon the mixture was stirred at 0° for 4 hours and at room temperature for 1 hour. The reaction mixture was concentrated in a high vacuum and the residue was chromatographed on 20 g of silica gel with chloroform/methanol (98:2), whereupon 95 mg (~100%) of tert.butyl (13S,16S,19R)-(13,16-dimethyl-12,15,18-trioxo-11,12,13,14,15,16,17,18,19,20,21,22-dodecahydro-1,19-etheno-10H-dibenz[b,o][1,5,8,11]-oxatriazacyclohexadecin-19-yl)-carbamate were obtained as a white powder. M.p. (dec.)=184°–186°. $[\alpha]_D = +34.0°$ (c=0.2, methanol).

EXAMPLE 4.5.7.a 3 ml of trifluoroacetic acid were added at 0° to a solution of 83 mg (0.155 mmol) of tert.butyl (13S,16S,19R)-(13,16-dimethyl-12,15,18-trioxo-11,12,13,14,15,16,17,18,19,20,21,22-dodecahydro-1,19-etheno-10H-dibenz[b,o][1,5,8,11]oxatriazacyclohexadecin-19-yl)-carbamate in 3 ml of dichloromethane, whereupon the mixture was stirred at 0° for 3 hours. The solvent was removed in a high vacuum and the residue was chromatographed on 15 g of silica gel with chloroform→chloroform/methanol (95:5), whereupon after drying in a high vacuum 71 mg (83.4%) of (13S,16S,19R)-19-amino-13,16-dimethyl-11,12,13,14,15,16,17,18,19,20,21,22-dodecahydro-1,19-etheno-10H-dibenz[b,o][1,5,8,11]-oxatriazacyclohexadecine-12,15,18-trione trifluoroacetate (1:1) were obtained as a white powder. M.p. 185°–188°. MS (ISP): 437.4 (M+H$^+$; 100).

EXAMPLE 5.1.1.a 14.0 μl (0.084 mmol) of ethyldiisopropylamine were added while cooling with ice and under argon to a solution of 10.0 mg (0.018 mmol) of (12S,15S,18R)-18-amino-12,15-dimethyl-10,11,12,13,14,15,16,17,18,19,20,21-dodecahydro-1,18-etheno-dibenz[b,n][1,5,8,11] oxatriazacyclopentadecine-11,14,17-trione trifluoroacetate (1:1), 6.8 mg (0.036 mmol) of Boc-L-alanine, 6.5 mg (0.048 mmol) of 1-hydroxy-7-pyridinotriazole (HOPT) and 11.5 mg (0.036 mmol) of 1,1,3,3-tetramethyl-2-[1H-1,2,3-triazolo[5,4-b]pyridin-1-yl]-uronium tetrafluoroborate (TATU) in 0.2 ml of N,N-dimethylformamide, whereupon the mixture was stirred at 0° for 15 hours. The reaction mixture was concentrated, the residue was taken up in water and chloroform, the organic phase was washed with water and concentrated, and the residue was chromatographed on 10 g of silica gel with chloroform→chloroform/methanol (98:2), whereupon after drying 10.0 mg (90.4%) of tert.butyl (S)-1-[(12S,15S,18R)-12,15-dimethyl-11,14,17-trioxo-10,11,12,13,14,15,16,17,18,19,20,21-dodecahydro-1,18-etheno-dibenz[b,n]-[1,5,8,11]oxatriazacyclopentadecin-18-ylcarbamoyl]-ethyl carbamate were obtained as a white solid. MS (LDP): 616.4 (M+Na$^+$; 100), 322.3 (52), 478.3 (50), 623.3 (43), 443.2 (41).

EXAMPLE 5.1.2.a 0.1 ml of trifluoroacetic acid was added at 0° under argon to a solution of 9.5 mg (0.016 mmol) of tert.butyl (S)-1-[(12S, 15S,18R)-12,15-dimethyl-11,14,17-trioxo-10,11,12,13,14,15,16,17,18,19,20,21-dodecahydro-1,18-etheno-dibenz[b,n][1,5,8,11]-oxatriazacyclopentadecin-18-ylcarbamoyl]-ethylcarbamate in 0.1 ml of dichloromethane, whereupon the mixture was stirred at 0° for 3 hours. The solvent was removed in a high vacuum and the residue was dried and re-precipitated with dichloromethane. After drying 11.0 mg (~100%) of (S)-2-amino-N-[(12S,15S,18R)-12,15-dimethyl-11,14,17-trioxo-10,11,12,13,14,15,16,17,18,19,20,21-dodecahydro-1,18-etheno-dibenz[b,n][1,5,8,11]-oxatriazacyclopentadecin-18-yl]-propionamide trifluoroacetate (1:1) were obtained as a white powder. MS (LDP): 494.6 (MH$^+$; 8), 516.5 (M+Na$^+$; 100), 532.4 (M+K$^+$; 34).

EXAMPLE 5.1.3.a 8.0 μl (0.048 mmol) of ethyldiisopropylamine were added dropwise to a solution of 11.0 mg (0.016 mmol) of (S)-2-amino-N-[(12S,15S,18R)-12,15-dimethyl-11,14,17-trioxo-10,11,12,13,14,15,16,17,18,19,20,21-dodecahydro-1,18-etheno-dibenz[b,n]-[1,5,8,11]-oxatriazacyclopentadecin-18-yl]-propionamide trifluoroacetate (1:1), 4.3 mg (0.032 mmol) of 3H-1,2,3-triazolo[4,5-b]pyridin-1-ol (HOAT), 7.7 mg (0.024 mmol) of 1,1,3,3-tetramethyl-2-[1H-1,2,3-triazolo[5,4-b]pyridin-1-yl]uronium tetrafluoroborate (TATU) and 18.7 mg (0.024 mmol) of p-bromobenzoyl-(Ala)$_2$-Aib-(Ala)$_5$-OH in 0.3 ml of N,N-dimethylformamide, whereupon the mixture was stirred at 0° for 15 hours. The reaction mixture was concentrated, the residue was taken up in water and chloroform, the organic phase was washed several times with water and concentrated, and the residue was chromatographed on 5 g of silica gel with chloroform→chloroform/methanol (95:5), whereupon after drying 18.5 mg (66.1%) of N-(4-bromo-benzoyl)-L-alanyl-L-alanyl-2-methyl-alanyl-L-alanyl-L-alanyl-L-alanyl-L-alanyl-L-alanyl-L-alanine (12S,15S,18R)-(12,15-dimethyl-11,14,17-trioxo-10,11,12,13,14,15,16,17,18,19,20,21-dodecahydro-1,18-etheno-dibenz[b,n][1,5,8,11]oxatriazacyclopentadecin-18-yl)-amide were obtained as a white solid. MS (LDP): 1260.4 (MH$^+$).

EXAMPLE 5.2.1.a

In analogy to Example 5.1.1.a, 40.0 mg (0.074 mmol) of (12S,15S,18R)-18-amino-12,15-dimethyl-10,11,12,13,14,15,16,17,18,19,20,21-dodecahydro-1,18-etheno-pyrido[2,3-b]benz[n]-[1,4,7,10]oxatriazacyclopentadecine-11,14,17-trione trifluoroacetate (1:1) in 2 ml of N,N-dimethylformamide were reacted at 0° for 20 hours with 20.8 mg (0.11 mmol) of Boc-L-alanine, 31.7 mg (0.166 mmol) of N-ethyl-N'-(3-dimethylaminopropyl)-carbodiimide, 22.0 mg (0.166 mmol) of 1-hydroxybenzotriazole and 12 μl (0.074 mmol) of ethyldiisopropylamine. Thereafter, a further 10.4 mg (0.055 mmol) of Boc-L-alanine, 16.0 mg (0.083 mmol) of N-ethyl-N'-(3-dimethylaminopropyl)-carbodiimide, 11.0 mg (0.083 mmol) of 1-hydroxybenzotriazole and 12 μl of ethyldiisopropylamine were added, whereupon the mixture was stirred for 8 hours. The reaction mixture was concentrated, the residue was taken up in ethyl acetate and water, the organic phase was washed with water, dried with Na$_2$SO$_4$ and concentrated, and the residue was chromatographed on 10 g of silica gel with chloroform/methanol (99:1), whereupon after drying in a high vacuum 35.0 mg (79.7%) of tert.butyl [(S)-1-[(12S,15S,18R)-12,15-dimethyl-11,14,17-trioxo-10,11,12,13,14,15,16,17,18,19,20,21-dodecahydro-1,18-etheno-pyrido[2,3-b]-benz[n][1,4,7,10]oxatriazacyclopentadecin-18-ylcarbamoyl]-ethyl]-carbamate were isolated as a white powder. M.p. (dec.)=233°–236°. [α]$_D$=−102.6° (c=0.8, methanol).

EXAMPLE 5.2.2.a 1.5 ml of trifluoroacetic acid were added at 0° under argon to a solution of 20.0 mg (0.034 mmol) of tert.butyl [(S)-1-[(12S,15S,18R)-12,15-dimethyl-11,14,17-trioxo-10,11,12,13,14,15,16,17,18,19,20,21-dodecahydro-1,18-etheno-pyrido[2,3-b]benz[n][1,4,7,10]-oxatriazacyclopentadecin-18-ylcarbamoyl]-ethyl]-carbamate in 1.5 ml of dichloromethane, whereupon the mixture was stirred at 0° for 3 hours. The solvent was removed in a high vacuum and the residue was suspended in 1 ml of water in an ultrasound bath and then lyophilized, whereupon after drying in a high vacuum 18.0 mg (87%) of (S)-2-amino-N-[(12S, 15S,18R)-12,15-dimethyl-11,14,17-trioxo-10,11,12,13,14,15,16,17,18,19,20,21-dodecahydro-1,18-etheno-pyrido[2,3-b]benz[n][1,4,7,10]oxatriazacyclopentadecin-18-yl]-propionamide trifluoroacetate (1:1) were obtained as a white powder. M.p. (dec.)=265°–267°. [α]$_D$=−98.2° (c=0.5, methanol).

EXAMPLE 5.2.3.a

In analogy to Example 5.1.3.a, 16.0 mg (26 μmol) of (S)-2-amino-N-[(12S,15S,18R)-12,15-dimethyl-11,14,17-trioxo- 10,11,12,13,14,15,16,17,18,19,20,21-dodecahydro-1,18-etheno-pyrido[2,3-b]benz[n][1,4,7,10]oxatriazacyclopentadecin-18-yl]-propionamide trifluoroacetate (1:1) in 1.5 ml of N,N-dimethylformamide were reacted at 0° for 3 hours with 30.6 mg (39.0 μmol) of p-bromobenzoyl-(Ala)$_2$-Aib-(Ala)$_5$-OH, 11.2 mg (58.5 μmol) of N-ethyl-N'-(3-dimethylaminopropyl)carbodiimide, 8.1 mg (60.0 μmol) of 1-hydroxybenzotriazole and 4.5 μl (20.0 μmol) of N-ethyl-diisopropylamine. The reaction mixture was concentrated in a high vacuum, the residue was taken up in chloroform and water, the organic phase was washed with water, dried with Na$_2$SO$_4$ and concentrated, and the residue was chromatographed on 5 g of silica gel with chloroform/methanol (95:5), whereupon after preparative HPLC chromatography (Vydac RP 18 column) 23.4 mg (72.0%) of N-(4-bromo-benzoyl)-L-alanyl-L-alanyl-2-methyl-alanyl-L alanyl-L-alanyl-L-alanyl-L-alanyl-L-alanine (12S,15S,18R)-(12,15-dimethyl-11,14,17-trioxo-10,11,12,13,14,15,16,17,18,19,20,21-dodecahydro-1,18-etheno-pyrido[2,3-b]benz[n][1,5,8,11]oxatriazacyclopentadecin-18-yl)-amide were obtained as a white powder. [α]$_D$=−57.5° (c=0.8, methanol). MS (ISP): 1259.8 (MH$^+$; 5), 659.2 (100), 642.4 (93), 631.4 (93).

EXAMPLE 5.3.1.a

In analogy to Example 5.1.1.a, 6.3 mg (12.2 μmol) of (3S,7S,10S,13R)-13-amino-3,7,10-trimethyl-3,4,5,6,7,8,9,10,11,12,13,14,19,20-tetradecahydro-13,15-etheno-2H-1,5,8,11-benzoxatriazacyclohexadecine-6,9,12-trione trifluoroacetate (1:1) were reacted at 0° for 4 hours with 3.4 mg (18.3 μmol) of Boc-L-alanine, 3.3 mg (24.4 μmol) of 3H-1,2,3-triazolo[4,5-b]pyridin-1-ol (HOAT), 5.89 mg (18.3 μmol) of 1,1,3,3-tetramethyl-2-[1H-1,2,3-triazolo[5,4-b]pyridin-1-yl]-uronium tetrafluoroborate (TATU) and 7.8 μl (45.7 μmol) of ethyldiisopropylamine in 0.3 ml of N,N-dimethylformamide, whereupon after chromatography of the residue on 5 g of silica gel with chloroform→chloroform/methanol (98:2) and drying in a high vacuum 8.2 mg (>100%) of tert.butyl [(S)-1-[(3S,7S,10S,13R)-3,7,10-trimethyl-6,9,12-trioxo-3,4,5,6,7,8,9,10,11,12,13,14,19,20-tetradecahydro-13,15-etheno-2H-1,5,8,11-benzoxatriazacyclohexadecin-13-ylcarbamoyl]-ethyl]-carbamate were obtained as a white residue. MS (LDP): 596.8 (M+Na$^+$; 100), 612.7 (M+K$^+$; 40), 357.5 (35), 495.1 (33).

EXAMPLE 5.3.2.a

In analogy to Example 5.1.2.a, 8.2 mg (12.2 μmol) of tert.butyl [(S)-1-[(3S,7S,10S,13R)-3,7,10-trimethyl-6,9,12-trioxo-3,4,5,6,7,8,9,10,11,12,13,14,19,20-tetradecahydro-13,15-etheno-2H-1,5,8,11-benzoxatriazacyclohexadecin-13-ylcarbamoyl]-ethyl]-carbamate were reacted in 0.3 ml of dichloromethane and 0.3 ml of trifluoroacetic acid at 0° for 4 hours, whereupon after precipitation from ether/hexane (1:1) and drying in a high vacuum the corresponding amine was obtained as the trifluoroacetate. 7.2 mg (12 μl) of this product were reacted with 14.3 mg (18.3 μmol) of p-bromobenzoyl-(Ala)$_2$-Aib-(Ala)$_5$-OH, 5.9 mg (18.3 μmol) of 1,1,3,3-tetramethyl-2-[1H-1,2,3-triazolo[5,4-b]pyridin-1-yl]uronium tetrafluoroborate (TATU), 3.3 mg (24.0 μmol) of 3H-1,2,3-triazolo[4,5-b]pyridin-1-ol (HOAT) and 7.8 μl (45.0 μmol) of ethyldiisopropylamine in 0.3 ml of N,N-dimethylformamide for 6 hours in analogy to Example 5.1.3.a. After working up according to Example 5.1.3.a the residue was chromatographed on 5 g of silica gel with chloroform→chloroform/methanol, whereupon after additional purification by means of preparative HPLC (Vydac RP-18) and drying in a high vacuum 5.2 mg (29.3%) of N-(4-bromo-benzoyl)-L-alanyl-L-alanyl-2-methyl-alanyl-L-alanyl-L-alanyl-L-alanyl-L-alanyl-L-alanyl-L-alanine (3S,7S,10S,13R)-(3,7,10-trimethyl-6,9,12-trioxo-3,4,5,6,7,8,9,10,11,12,13,14,19,20-tetradecahydro-13,15-etheno-2H-1,5,8,11-benzoxatriazacyclohexadecin-13-yl)-amide were obtained as a white powder. MS (LDP): 1240.3 (M+H$^+$; 100), 374.0 (31), 391.9 (23), 411.1 (23).

EXAMPLE 5.4.1.a

In analogy to Example 5.1.1.a, 10.0 mg (18.4 μmol) of (3S,7S,10S,13R)-13-amino-5-ethyl-3,7,10-trimethyl-3,4,5,6,7,8,9,10,11,12,13,14,19,20-tetradecahydro-2H-1,5,8,11-benzoxatriazacyclohexadecine-6,9,12-trione trifluoroacetate (1:1) were reacted at 0° for 15 hours with 5.2 mg (27.6 μmol) of Boc-L-alanine, 5.0 mg (36.8 μmol) of 3H-1,2,3-triazolo[4,5-b]pyridin-1-ol (HOAT), 8.9 mg (27.6 μmol) of 1,1,3,3-tetramethyl-2-[1H-1,2,3-triazolo[5,4-b]pyridin-1-yl]-uronium tetrafluoroborate (TATU) and 11 μl (64.0 μmol) of ethyldiisopropylamine in 0.5 ml of N,N-dimethylformamide, whereupon working up and purification was carried out according to Example 5.1.1.a. After chromatography on 10 g of silica gel with chloroform→chloroform/methanol (95:5) and drying in a high vacuum 9.5 mg (86.4%) of tert.butyl [(S)-1-[(3S,7S,10S,13R)-5-ethyl-3,7,10-trimethyl-6,9,12-trioxo-13,15-etheno-3,4,5,6,7,8,9,10,11,12,13,14,19,20-tetradecahydro-2H-1,5,8,11-benzoxatriazacyclohexadecin-13-ylcarbamoyl]-ethyl]-carbamate were obtained as a white powder. MS (ISP): 602.4 (M+H$^+$; 100).

EXAMPLE 5.4.2.a

In analogy to Example 5.1.2.a, 9.5 mg (16.0 μmol) of tert.butyl [(S)-1-[(3S,7S,10S,13R)-5-ethyl-3,7,10-trimethyl-6,9,12-trioxo-13,15-etheno-3,4,5,6,7,8,9,10,11,12,13,14,19,20-tetradecahydro-2H-1,5,8,11-benzoxatriazacyclohexadecin-13-ylcarbamoyl]-ethyl]-carbamate were reacted in 0.1 ml of dichloromethane and 0.1 ml of trifluoroacetic acid at 0° for 2 hours, whereupon the mixture was worked up according to Example 5.1.2.a. The residue was chromatographed on silica gel with chloroform/methanol (95:5→4:1), whereupon after drying in a high vacuum 9.2 mg (94.8%) of (S)-2-amino-N-[(3S,7S,10S,13R)-5-ethyl-3,7,10-trimethyl-6,9,12-trioxo-13,15-etheno-3,4,5,6,7,8,9,10,11,12,13,14,19,20-tetradecahydro-2H-1,5,8,11-benzoxatriazacyclohexadecin-13-yl]-propionamide trifluoroacetate (1:1) were obtained as a white powder. MS (ISP): 502.5 (M+H$^+$; 34), 267.4 (100), 289.4 (44), 211 (26), 279.3 (20).

EXAMPLE 5.4.3.a

In analogy to Example 5.1.3.a, 9.2 mg (14.9 μmol) of (S)-2-amino-N-[(3S,7S,10S,13R)-5-ethyl-3,7,10-trimethyl-6,9,12-trioxo-13,15-etheno-3,4,5,6,7,8,9,10,11,12,13,14,19,20-tetradecahydro-2H-1,5,8,11-benzoxatriazacyclohexadecin-13-yl]-propionamide trifluoroacetate (1:1) were reacted at 0° for 15 hours with 21.5 mg (27.5 μmol) of p-bromobenzoyl-(Ala)$_2$-Aib-(Ala)$_5$-OH, 8.8 mg (27.5 μmol) of 1,1,3,3-tetramethyl-2-[1H-1,2,3-triazolo[5,4-b]pyridin-1-yl]-uronium tetrafluoroborate (TATU), 4.0 mg (29.8 μmol) of 3H-1,2,3-triazolo[4,5-b]pyridin-1-ol (HOAT) and 8.9 μl (52.1 μmol) of ethyldiisopropylamine in 0.3 ml of N,N-dimethylformamide. Subsequently, the mixture was worked up according to Example 5.1.3.a and the residue was chromatographed on 10 g of silica gel with chloroform/methanol (99:1→95:5), whereupon after drying in a high vacuum 14.0 mg (74%) of N-(4-bromo-benzoyl)-L-alanyl-Lalanyl-2-methyl-alanyl-L-alanyl-L-alanyl-L-alanyl-L-alanyl-L-alanyl-L-alanine (3S,7S,10S,13R)-(5-ethyl-3,7,10-trimethyl-6,9,12-trioxo-13,15-etheno-3,4,5,6,7,8,9,10,11,12,13,14,19,20-tetradecahydro-2H-1,5,8,11-benzoxatriazacyclohexadecin-13-yl)-amide were obtained as a light beige solid. MS (LDP): 1267.5 (M+H$^+$; 100), 1093.3 (22), 1191,5 (8), 1120.5 (8), 552.1 (8).

EXAMPLE 5.5.1.a

In analogy to Example 5.2.1.a, 63 mg (0.114 mmol) of (13S,16S,19R)-19-amino-13,16-dimethyl-11,12,13,14,15,16,17,18,19,20,21,22-dodecahydro-1,19-etheno-10H-dibenz[b,o][1,5,8,11]oxatriazacyclohexadecine-12,15,18-trione trifluoroacetate (1:1) in 2 ml of N,N-dimethylformamide were reacted at 0° for 24 hours with 32.0 mg (0.171 mmol) of Boc-L-alanine, 39 mg (0.256 mmol) of 1-hydroxybenzotriazole, 49 mg (0.256 mmol) of N-ethyl-N'(3-dimethylaminopropyl)carbodiimide hydrochloride and 86 μl (0.53 mmol) of ethyldiisopropylamine, whereupon after chromatography of the residue on 5 g of silica gel with chloroform/methanol (95:5) ~70 mg (100%) of tert.butyl [(S)-1[(13S,16S,19R)-13,16-dimethyl-12,15,18-trioxo-11,12,13,14,15,16,17,18,19,20,22-dodecahydro-1,19-etheno-10H-dibenz-[b,o][1,5,8,11]oxatriazacyclohexadecin-19-ylcarbamoyl]-ethyl]-carbamate were obtained as a white powder. M.p. 245°–246°. [α]$_D$=+46.5° (c=0.2, methanol).

EXAMPLE 5.5.2.a

In analogy to Example 5.1.2.a , 70 mg (0.115 mmol) of tert.butyl [(S)-1-[(13S,16S,19R)-13,16-dimethyl-12,15,18-trioxo-11,12,13,14,15,16,17,18,19,20,22-dodecahydro-1,19-etheno-10-dibenz[b,o][1,5,8,11]oxatriazacyclohexadecin-19-ylcarbamoyl]-ethyl]-carbamate in 2 ml of dichloromethane were reacted with 2 ml of trifluoroacetic acid, whereupon after chromatography of the residue on 10 g of silica gel with chloroform/methanol (95:5) and drying in a high vacuum 54 mg (75.4%) of (S)-2-amino-N-[(13S,16S,19R)-13,16-dimethyl-12,15,18-trioxo-11,12,13,14,15,16,17,18,19,20,21,22-dodecahydro-1,19-etheno-10H-dibenz[b,o][1,5,8,11]oxatriazacyclohexadecin-19-yl]-propionamide trifluoroacetate (1:1) were obtained as a white powder. M.p. 202°–204°. MS (ISP): 508.4 (M+H$^+$; 100).

EXAMPLE 5.5.3.a

In analogy to Example 5.1.3.a, 45.0 mg (72 μmol) of (S)-2-amino-N-[(13S,16S,19R)-13,16-dimethyl-12,15,18-trioxo-11,12,13,14,15,16,17,18,19,20,21,22-dodecahydro-1,19-etheno-10H-dibenz[b,o][1,5,8,11]oxatriazacyclohexadecin-19-yl]-propionamide trifluoroacetate (1:1) were reacted at room temperature for 15 hours with 84.7 mg (0.108 mmol) of p-bromobenzoyl-(Ala)$_2$-Aib-(Ala)$_5$-OH, 21.8 mg (0.162 mmol) of 1-hydroxybenzotriazole, 31.0 mg (0.162 mmol) of N-ethyl-N'-(3-dimethylaminopropyl)carbodiimide hydrochloride and 18 μl (0.108 mmol) of ethyldiisopropylamine in 2.5 ml of N,N-dimethylformamide, whereupon after chromatography of the residue on 15 g of silica gel with chloroform/methanol (95:5) and recrystallization from acetonitrile 24 mg (26.1%) of N-(4-bromobenzoyl)-L-alanyl-L-alanyl-2-methyl-alanyl-L-alanyl-L-alanyl-L-alanyl-L-alanyl-L-alanyl-L-alanine (13S,16S,19R)-(13,16-dimethyl-12,15,18-trioxo-11,12,13,14,15,16,17,18,19,20,21,22-dodecahydro-1,19-etheno-10H-dibenz[b,o][1,5,8,11]oxatriazacyclohexadecin-19-yl)-amide were obtained as a white powder. M.p. 285°–288° (dec.). MS (ISP): 1274.6 (M+H$^+$; 30), 665.8 (100), 686.4 (95). 707 (65), 638 (40).

We claim:

1. A tetrahydronaphthalene compound of the formula

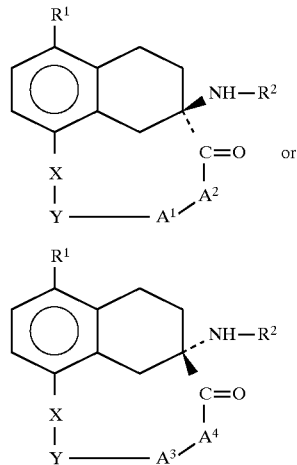

wherein
R$^1$ is hydrogen, bromine, cyano, formyl, hydroxy, lower alkyl, lower alkenyl, lower alkynyl, lower alkoxy, aryloxy, lower aralkoxy or aryl;
R$^2$ is an amino acid residue or a chain of 2 to 20 amino acid residues wherein reactive moieties in the side chains of the amino acid residue(s) is/are protected or unprotected, and wherein the amino group of the N-terminal amino acid is a free or protected amino group;

$A^1$, $A^2$, $A^3$ and $A^4$ each are α-amino acid residues wherein $A^1$ and $A^2$ are in the L configuration and $A^3$ and $A^4$ are in the D configuration when the α-C atom of said α-amino acid residue is asymmetric;

X is oxygen or sulphur;

Y is a residue of the formula

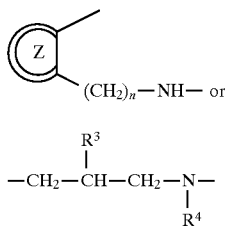

n is 0 or 1;

$R^3$ is hydrogen or lower alkyl;

$R^4$ is hydrogen or lower alkyl; and

Z and the two C atoms together are an aromatic ring selected from the group consisting of benzene, furan, thiophene, pyridine or pyrimidine, wherein said aromatic ring is substituted or unsubstituted; and salts thereof.

2. A compound of claim 1, wherein $R^1$ is hydrogen.

3. A compound of claim 1 wherein $R^1$ is phenyl mono- or disubstituted by lower alkyl or lower alkoxy or phenyl substituted by lower alkylenedioxy.

4. A compound of claim 1 wherein $R^2$ is 9 to 15 amino acid residues.

5. A compound of claim 1 wherein $R^2$ is 9, 12 or 15 amino acid residues.

6. A compound of claim 5 wherein any amino acid residues of $R^2$ which are α-amino acids, are in the L configuration when the α-C atom of said amino acid is asymmetric.

7. A compound of claim 6 wherein $R^2$ comprises one or more residues selected from the group consisting of L-alanine, L-glutamine, L-glutamic acid, L-isoleucine, L-leucine, L-lysine and 2-amino-2-methylproprionic acid.

8. A compound of claim 7 wherein $A^1$ is a residue of L-alanine, asparagine, aspartic acid, glutamine, glutamic acid, lysine or of 2-amino-2-methylpropionic acid; $A^3$ is a residue of D-alanine, asparagine, aspartic acid, glutamine, glutamic acid or lysine or of 2-amino-2-methylpropionic acid; $A^2$ is a residue of L-alanine, asparagine, aspartic acid, glutamine, glutamic acid or lysine; and $A^4$ is a residue of D-alanine, asparagine, aspartic acid, glutamine, glutamic acid or lysine.

9. A compound of claim 8 wherein $A^1$ and $A^2$ are L-alanyl and $A^3$ and $A^4$ are D-alanyl.

10. A compound of claim 9 wherein Y is a residue of formula (a), n is 0 and Z and the two C atoms together are benzene.

11. A compound of claim 9 wherein $R^1$ is hydrogen and X is oxygen.

12. A compound of claim 11 wherein the amino group of the N-terminal amino acid of $R^2$ is a protected amino group.

13. A compound of claim 12 wherein the protected amino group is protected with para-bromo-benzoyl.

14. A compound of claim 13 wherein Y is a residue of formula (b).

15. A compound of claim 13 wherein Y is a residue of formula (a).

16. A compound of claim 15 wherein Z and the two C atoms together are benzene.

17. A compound of claim 15 wherein Z and the two C atoms together are pyrimidine.

18. A compound of claim 16 which is N-(4-Bromo-benzoyl)-L-alanyl-L-alanyl-2-methyl-alanyl-L-alanyl-L-alanyl-L-alanyl-L-alanyl-L-alanyl-L-alanine (12S,15S,18R)-(12,15-dimethyl-11,14,17-trioxo-10,11,12,13, 14,15,16,17,18,19,20,21-dodecahydro-1,18-etheno-dibenz[b,n][1,5,8,11]oxatriazacyclopentadecin-18-yl)-amide.

19. A compound of claim 17 which is N-(4-bromo-benzoyl)-L-alanyl-L-alanyl-2-methyl-alanyl-L-alanyl-L-alanyl-L-alanyl-L-alanyl-L-alanyl-L-alanine (12S, 15S, 18R)-(12,15-dimethyl-11,14,17-trioxo-10,11,12,13,14,15, 16,17,18,19,20,21-dodecahydro-1,18-etheno-pyrido[2,3-b] benz[n][1,5,8,11]oxatriazacyclopentadecin-18-yl)-amide.

20. A compound of claim 14 which is N-(4-bromo-benzoyl)-L-alanyl-L-alanyl-2-methyl-alanyl-L-alanyl-L-alanyl-L-alanyl-L-alanyl-L-alanyl-L-alanine (3S, 7S,10S, 13R)-(3,7,10-trimethyl-6,9,12-trioxo-3,4,5,6,7,8,9,10,11, 12,13,14,19,20-tetradecahydro-13,15-etheno-2H-1,5,8,11-benzoxatriazacyclohexadecin-13-yl)-amide.

21. A compound of claim 14 which is N-(4-bromo-benzoyl)-L-alanyl-L-alanyl-2-methyl-alanyl-L-alanyl-L-alanyl-L-alanyl-L-alanyl-L-alanyl-L-alanine (3S, 7S,10S, 13R)-(5-ethyl-3,7,10-trimethyl-6,9,12-trioxo-13,15-etheno-3,4,5,6,7,8,9,10,11,12,13,14,19,20-tetradecahydro-2H-1,5, 8,11-benzoxatriazacyclohexadecin-13-yl)-amide.

22. A compound of claim 16 which is N-(4-bromo-benzoyl)-L-alanyl-L-alanyl-2-methyl-alanyl-L-alanyl-L-alanyl-L-alanyl-L-alanyl-L-alanyl-L-alanine (13S, 16S, 19R)-(13,16-dimethyl-12,15,18-trioxo-11,12,13,14,15,16, 17,18,19,20,21,22-dodecahydro-1,19-etheno-10H-dibenz[b, o][1,5,8,11]oxatriazacyclohexadecin-19-yl)-amide.

23. A compound of the formula

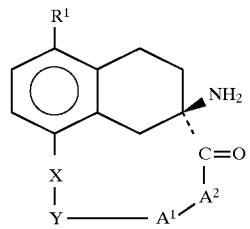

or

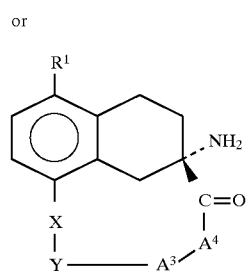

wherein $R^1$ is hydrogen, bromine, cyano, formyl, hydroxy, lower alkyl, lower alkenyl, lower alkynyl, lower alkoxy, aryloxy, lower aralkoxy or aryl;

$A^1$, $A^2$, $A^3$ and $A^4$ each are α-amino acid residues wherein $A^1$ and $A^2$ are in the L configuration and $A^3$ and $A^4$ are in the D configuration when the (α-C atom of said (α-amino acid residue is asymmetric;

X is oxygen or sulphur;
Y is a residue of the formula

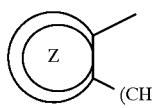 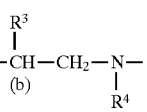

n is 0 or 1;
R³ is hydrogen or lower alkyl;
R⁴ is hydrogen or lower alkyl; and
Z and the two C atoms together are an aromatic ring selected from the group consisting of benzene, furan, thiophene, pyridine or pyrimidine, wherein said aromatic ring is substituted or unsubstituted.

24. A compound of claim 23 wherein R¹ is aryl.

25. A compound of claim 23 wherein R¹ is hydrogen.

26. A compound of claim 24 wherein R¹ is phenyl mono- or disubstituted by lower alkyl or lower alkoxy or phenyl substituted by lower alkylenedioxy.

27. A compound of claim 23 wherein A¹ is a residue of L-alanine, asparagine, aspartic acid, glutamine, glutamic acid, lysine or of 2-amino-2-methylpropionic acid; A³ is a residue of D-alanine, asparagine, aspartic acid, glutamine, glutamic acid or lysine or of 2-amino-2-methylpropionic acid; A² is a residue of L-alanine, asparagine, aspartic acid, glutamine, glutamic acid or lysine; and A⁴ is a residue of D-alanine, asparagine, aspartic acid, glutamine, glutamic acid or lysine.

28. A compound of claim 27 wherein A¹ and A² are L-alanyl and A³ and A⁴ are D-alanyl.

29. A compound of claim 23 wherein Y is a residue of formula (a), n is 0 and Z and the two C atoms together are a benzene ring.

30. A compound of the formula

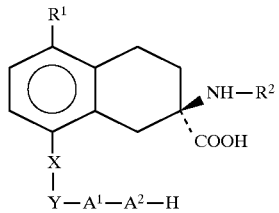   IIIa or

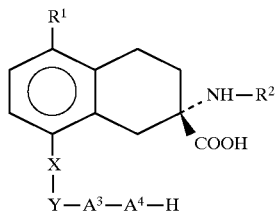   IIIb wherein R¹ is hydrogen, bromine, cyano, formyl, hydroxy, lower alkyl, lower alkenyl, lower alkynyl, lower alkoxy, aryloxy, lower aralkoxy or aryl;
R² is an amino acid residue or a chain of 2 to 20 amino acid residues wherein reactive moieties in the side chains of the amino acid residue(s) is/are protected or unprotected, and wherein the amino group of the N-terminal amino acid is a free or protected amino group;
A¹, A², A³ and A⁴ each are α-amino acid residues wherein A¹ and A² are in the L configuration and A³ and A⁴ are in the D configuration when the α-C atom of said α-amino acid residue is asymmetric;

X is oxygen or sulphur;
Y is a residue of the formula

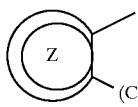 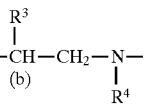

n is 0 or 1;
R³ is hydrogen or lower alkyl;
R⁴ is hydrogen or lower alkyl; and
Z and the two C atoms together are an aromatic ring selected from the group consisting of benzene, furan, thiophene, pyridine or pyrimidine, wherein said aromatic ring is substituted or unsubstituted.

31. A compound of claim 30 wherein R¹ is hydrogen.

32. A compound of claim 30 wherein R¹ is aryl.

33. A compound of claim 32 wherein R¹ is phenyl mono- or disubstituted by lower alkyl or lower alkoxy or phenyl substituted by lower alkylenedioxy.

34. A compound of claim 30 wherein R² is 9 to 15 amino acid residues.

35. A compound of claim 34 wherein R² is 9, 12 or 15 amino acid residues.

36. A compound of claim 30 wherein any amino acid residues of R² which are α-amino acids, are in the L configuration when the α-C atom of said amino acid is asymmetric.

37. A compound of claim 36 wherein R² comprises one or more residues selected from the group consisting of L-alanine, L-glutamine, L-glutamic acid, L-isoleucine, L-leucine, L-lysine and 2-amino-2-methylproprionic acid.

38. A compound of claim 37 wherein A¹ is a residue of L-alanine, asparagine, aspartic acid, glutamine, glutamic acid, lysine or of 2-amino-2-methylpropionic acid; A³ is a residue of D-alanine, asparagine, aspartic acid, glutamine, glutamic acid or lysine or of 2-amino-2-methylpropionic acid; A² is a residue of L-alanine, asparagine, aspartic acid, glutamine, glutamic acid or lysine; and A⁴ is a residue of D-alanine, asparagine, aspartic acid, glutamine, glutamic acid or lysine.

39. A compound of claim 38 wherein A¹ and A² are L-alanyl and A³ and A⁴ are D-alanyl.

40. A compound of claim 30 wherein Y is a residue of formula (a), n is 0 and Z and the two C atoms together are a benzene ring.

41. A compound of the formula:

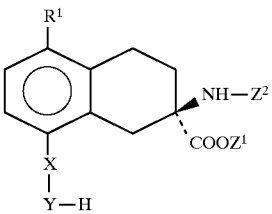   IVa or

-continued

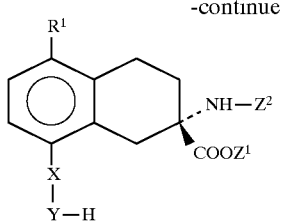

IVb wherein R¹ is hydrogen, bromine, cyano, formyl, hydroxy, lower alkyl, lower alkenyl, lower alkynyl, lower alkoxy, aryloxy, lower aralkoxy or aryl;

X is oxygen or sulphur;

Y is a residue of the formula

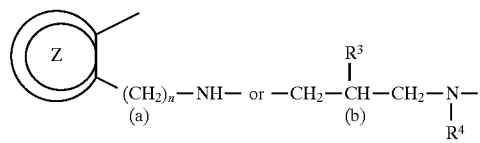

n is 0 or 1;

R³ is hydrogen or lower alkyl;

R⁴ is hydrogen or lower alkyl; and Z and the two C atoms together are an aromatic ring selected from the group consisting of benzene, furan, thiophene, pyridine or pyrimidine, wherein said aromatic ring is substituted or unsubstituted;

Z¹ is a carboxyl protecting group; Z² is an amino protecting group.

42. A compound of claim 41 wherein R¹ is hydrogen.

43. A compound of claim 41 wherein R¹ is aryl.

44. A compound of claim 43 wherein R¹ is phenyl mono- or disubstituted by lower alkyl or lower alkoxy or phenyl substituted by lower alkylenedioxy.

45. A compound of claim 41 wherein Y is a residue of formula (a), n is 0 and Z and the two C atoms together are a benzene ring.

46. A compound of claim 41 wherein Z¹ is methyl, tert.butyl, benzyl, trimethylsilylethyl or pentafluorophenyl and Z² is benzyloxycarbonyl, tert.butyloxycarbonyl or fluoren-9-ylmethoxycarbonyl.

47. A process for the manufacture of compounds of claim 1, which process comprises a) coupling a compound of claim 23 with an amino acid residue or a chain of 2 to 20 amino acid residues wherein reactive moieties in the side chains of the amino acid residue(s) is/are protected or unprotected, and wherein the amino group of the N-terminal amino acid is a free or protected amino group; or b) cyclizing a compound of claim 30 or c) cleaving off the protecting group(s) from a compound of claim 1 which contains at least one protecting group; or d) converting a compound of claim 1 which contains a basic centre into a salt using an acid or a compound of claim 1 which contains an acidic centre into a salt using a base.

* * * * *